(12) United States Patent
Humpston et al.

(10) Patent No.: US 12,067,711 B2
(45) Date of Patent: Aug. 20, 2024

(54) DATA PROCESSING PLATFORM FOR ANALYZING STEREO-SPATIO-TEMPORAL CROP CONDITION MEASUREMENTS TO SUPPORT PLANT GROWTH AND HEALTH OPTIMIZATION

(71) Applicant: Ecoation Innovative Solutions Inc., North Vancouver (CA)

(72) Inventors: Stephen P. Humpston, Much Wenlock (GB); Gregory E. Stewart, North Vancouver (CA); Gavin Schneider, North Vancouver (CA); Adrian M. Fuxman, North Vancouver (CA); Patrick O. Wspanialy, Mississauga (CA); Saber Miresmailli, North Vancouver (CA)

(73) Assignee: Ecoation Innovative Solutions Inc., North Vancouver (CA)

( * ) Notice: Subject to any disclaimer, the term of this patent is extended or adjusted under 35 U.S.C. 154(b) by 83 days.

(21) Appl. No.: 17/098,172

(22) Filed: Nov. 13, 2020

(65) Prior Publication Data
US 2022/0156921 A1    May 19, 2022

(51) Int. Cl.
*A01G 7/00* (2006.01)
*G01N 33/00* (2006.01)
(Continued)

(52) U.S. Cl.
CPC .............. *G06T 7/0012* (2013.01); *A01G 7/00* (2013.01); *G01N 33/0098* (2013.01);
(Continued)

(58) Field of Classification Search
CPC ........ G06V 20/188; G06V 10/62; A01G 7/00; A01G 9/14; A01G 7/06; Y02A 40/25;
(Continued)

(56) References Cited

U.S. PATENT DOCUMENTS 4,755,942 A   7/1988   Gardner et al.
4,876,647 A   10/1989  Gardner et al.
(Continued)

FOREIGN PATENT DOCUMENTS

CN    108106673 A    6/2018
CN    209181816 U    7/2019
(Continued)

OTHER PUBLICATIONS

International Search Report and Written Opinion of the International Searching Authority dated Oct. 4, 2021 in connection with International Patent Application No. PCT/CA2021/051041, 9 pages.
(Continued)

*Primary Examiner* — Sumati Lefkowitz
*Assistant Examiner* — Michael Adam Shariff

(57) ABSTRACT

An apparatus includes at least one processor configured to obtain stereo-spatio-temporal data measurements of plants in a growing area. The stereo-spatio-temporal data measurements include (i) first spatio-temporal data measurements of the plants in the growing area and (ii) second spatio-temporal data measurements of the plants in the growing area. The at least one processor is also configured to analyze the stereo-spatio-temporal data measurements to identify one or more actual or potential problems associated with one or more of the plants. The at least one processor is further configured to generate a graphical user interface identifying at least one of the one or more actual or potential problems with the one or more plants. The first and second spatio-temporal data measurements of each stereo-spatio-temporal data measurement are associated with at least one common plant characteristic and different three-dimensional positions within the growing area taken at one or more known times.

30 Claims, 14 Drawing Sheets

(51) Int. Cl.
*G06T 7/00* (2017.01)
*G06V 20/10* (2022.01)

(52) U.S. Cl.
CPC ........ *G06V 20/188* (2022.01); *G06T 2200/24* (2013.01); *G06T 2207/10021* (2013.01); *G06T 2207/10036* (2013.01)

(58) Field of Classification Search
CPC . G06T 2207/30188; G06T 2207/10021; G06T 2207/10036; G06T 2200/24; G01N 2021/8466; G01N 33/0098; G01N 2035/0091; G01B 11/0608; G06F 2206/1008
See application file for complete search history.

(56) References Cited

U.S. PATENT DOCUMENTS

| | | |
|---|---|---|
| 5,130,545 A | 7/1992 | Lussier |
| 5,839,106 A | 11/1998 | Bellegarda |
| 6,397,162 B1 | 5/2002 | Ton |
| 6,573,512 B1 | 6/2003 | Lucia et al. |
| 6,657,117 B2 | 12/2003 | Weare et al. |
| 6,701,665 B1 | 3/2004 | Ton et al. |
| 7,112,806 B2 | 9/2006 | Lussier |
| 7,412,330 B2 | 8/2008 | Spicer et al. |
| 7,487,925 B2 | 2/2009 | Skinner |
| 7,617,057 B2 | 11/2009 | May et al. |
| 7,715,013 B2 | 5/2010 | Glaser et al. |
| 7,987,632 B2 | 8/2011 | May et al. |
| 8,028,470 B2 | 10/2011 | Anderson |
| 8,061,080 B2 | 11/2011 | Loebl et al. |
| 8,249,308 B2 | 8/2012 | Lussier |
| 8,437,498 B2 | 5/2013 | Malsam |
| 8,437,879 B2 | 5/2013 | Anderson |
| 8,476,603 B2 | 7/2013 | Moise et al. |
| 8,504,234 B2 | 8/2013 | Anderson |
| 8,836,504 B2 | 9/2014 | Kohler et al. |
| 9,532,411 B2 | 12/2016 | Conrad et al. |
| 9,576,786 B2 | 2/2017 | Greenberg et al. |
| 9,939,132 B2 | 4/2018 | Greenberg et al. |
| 9,992,991 B2 | 6/2018 | Cink et al. |
| 10,021,837 B2 | 7/2018 | Greenberg et al. |
| 10,241,097 B2 * | 3/2019 | Miresmailli ........... G01D 11/30 |
| 10,339,380 B2 | 7/2019 | Greenberg et al. |
| 10,627,785 B2 | 4/2020 | King et al. |
| 10,635,274 B2 | 4/2020 | Greenberg et al. |
| 10,701,852 B2 | 7/2020 | Calleija et al. |
| 10,791,037 B2 | 9/2020 | Greenberg et al. |
| 10,871,480 B2 | 12/2020 | Miresmailli et al. |
| 10,929,664 B2 | 2/2021 | King |
| 10,949,974 B2 | 3/2021 | King et al. |
| 11,003,456 B2 | 5/2021 | King |
| 11,062,516 B2 | 7/2021 | Greenberg et al. |
| 2002/0167587 A1 | 11/2002 | Ogasawara |
| 2002/0170229 A1 | 11/2002 | Ton et al. |
| 2003/0229497 A1 | 12/2003 | Wilson et al. |
| 2004/0241635 A1 | 12/2004 | Buckley |
| 2011/0101239 A1 | 5/2011 | Woodhouse et al. |
| 2011/0261355 A1 | 10/2011 | Hannel et al. |
| 2012/0046837 A1 | 2/2012 | Anderson |
| 2012/0101861 A1 | 4/2012 | Lindores |
| 2012/0109387 A1 | 5/2012 | Martin et al. |
| 2012/0113225 A1 | 5/2012 | Deppermann et al. |
| 2012/0114187 A1 | 5/2012 | Duarte |
| 2012/0150355 A1 | 6/2012 | Anderson |
| 2014/0035752 A1 | 2/2014 | Johnson |
| 2014/0059722 A1 | 2/2014 | Krichevsky |
| 2014/0064568 A1 | 3/2014 | Moon et al. |
| 2014/0180549 A1 | 6/2014 | Siemens et al. |
| 2014/0222374 A1 | 8/2014 | Lock et al. |
| 2015/0027040 A1 | 1/2015 | Redden |
| 2017/0030877 A1 | 2/2017 | Miresmailli et al. |
| 2017/0032258 A1 | 2/2017 | Miresmailli et al. |
| 2017/0172075 A1 | 6/2017 | Bermudez Rodriguez et al. |
| 2017/0176595 A1 | 6/2017 | McPeek |
| 2017/0332544 A1 | 11/2017 | Conrad et al. |
| 2017/0359943 A1 | 12/2017 | Calleija et al. |
| 2018/0082362 A1 | 3/2018 | Greenberg et al. |
| 2018/0082375 A1 | 3/2018 | Greenberg et al. |
| 2019/0050948 A1 | 2/2019 | Perry et al. |
| 2019/0098842 A1 | 4/2019 | Barber, III et al. |
| 2019/0170718 A1 | 6/2019 | Miresmailli et al. |
| 2019/0200535 A1 | 7/2019 | Regan et al. |
| 2019/0244428 A1 | 8/2019 | Greenberg et al. |
| 2020/0019777 A1 * | 1/2020 | Gurzoni, Jr. ......... G06V 10/803 |
| 2020/0325005 A1 | 10/2020 | Zhang et al. |
| 2020/0380616 A1 | 12/2020 | King et al. |
| 2021/0048822 A1 | 2/2021 | Miresmailli |
| 2021/0072210 A1 | 3/2021 | Miresmaili et al. |
| 2021/0133443 A1 * | 5/2021 | Gurzoni et al. ..... A01B 79/005 |
| 2021/0298244 A1 | 9/2021 | King et al. |
| 2021/0302973 A1 | 9/2021 | King et al. |
| 2021/0304216 A1 | 9/2021 | King et al. |
| 2021/0304326 A1 | 9/2021 | Greenberg et al. |
| 2021/0350295 A1 * | 11/2021 | Singh et al. ....... G06Q 10/0635 |
| 2022/0130036 A1 * | 4/2022 | Gatto ..................... G06T 7/70 |

FOREIGN PATENT DOCUMENTS

| | | |
|---|---|---|
| CN | 111089829 A | 5/2020 |
| DE | 10148747 A1 | 4/2003 |
| EP | 3491613 A1 | 6/2019 |
| IN | 202041012385 A | 5/2020 |
| JP | 6963102 B2 | 11/2021 |
| WO | 2009141465 A1 | 11/2009 |
| WO | 2018057799 A1 | 3/2018 |
| WO | 2018203337 A1 | 11/2018 |
| WO | 2019134454 A1 | 7/2019 |
| WO | 2019144231 A1 | 8/2019 |

OTHER PUBLICATIONS

International Search Report and Written Opinion of the International Searching Authority dated Nov. 2, 2021 in connection with International Patent Application No. PCT/CA2021/051039, 10 pages.
International Search Report and Written Opinion of the International Searching Authority dated Nov. 1, 2021 in connection with International Patent Application No. PCT/CA2021/051043, 10 pages.
Dong et al., "4D Crop Monitoring: Spatio-Temporal Reconstruction for Agriculture," 2017 IEEE International Conference on Robotics and Automation, IEEE, 2017, 8 pages.
Wijanarko et al., "Development of Mobile RoboVision with Stereo Camera for Automatic Crop Growth Monitoring in Plant Factory," International Conference on Science and Applied Science, AIP Conference Proceeding 2202, 020100-1-020100-7, Dec. 2019, 8 pages.
Bendig et al., "Combining UAV-based plant height from crop surface models, visible, and near infrared vegetation indices for biomass monitoring in barley," International Journal of Applied Earth Observation and Geoinformation, Mar. 2015, 9 pages.
Jansen et al., "Induced plant volatiles allow sensitive monitoring of plant health status in greenhouses," Plant Signaling Behavior, 2009, p. 824-829.
Koppert Biological Systems, "Airbug," Product Specification, Apr. 2020, 3 pages.
Koppert Biological Systems, "Biological pest management to ensure healthy crops," Product List, Dec. 2016, 1 page.
Mandow et al., "The Autonomous Mobile Robot AURORA for Greenhouse Operation," IEEE Robotics and Automation Magazine, Dec. 1996, 11 pages.
Nicolai et al., "Nondestructive measurement of fruit and vegetable quality by means of NIR spectroscopy: A review," Science Direct, Postharvest Biology and Technology 46, 2007, p. 99-118.
Ruiz-Altisent et al., "Sensors for product characterization and quality of specialty crops—A review," Computers and Electronics in Agriculture 74, 2010, p. 176-194.
Sankaran et al., "A review of advanced techniques for detecting plant diseases," Computer and Electronics in Agriculture, vol. 72, Jun. 2010, pp. 1-13.

(56) References Cited

OTHER PUBLICATIONS

Story et al., "Automated Machine Vision Guided Plant Monitoring System for Greenhouse Crop Diagnostics," Acta Hortic, 1037, 2014, p. 636-641 (abstract only).
Ton et al., "Phytomonitoring: A Bridge from Sensors to Information Technology for Greenhouse Control," Phytech Ltd., 2003, p. 639-644.
International Search Report and Written Opinion of the International Searching Authority in connection with International Patent Application No. PCT/CA2020/051099 dated Nov. 6, 2020, 11 pages.
Office Action dated Jul. 1, 2020 in connection with U.S. Appl. No. 16/268,744, 20 pages.
Office Action dated Mar. 11, 2020 in connection with U.S. Appl. No. 15/219,328, 21 pages.
Final Office Action dated Sep. 18, 2020 in connection with U.S. Appl. No. 15/219,328, 24 pages.
Office Action dated Jan. 6, 2021 in connection with U.S. Appl. No. 15/219,328, 28 pages.
30MHz, "Data should work for the grower (and that means working together)," Oct. 2020, 3 pages.
30MHz, "The Data platform for horticulture—30MHz," Oct. 2020, 13 pages.
30MHz, "Wireless sensors built for horticulture," Sensors, Oct. 2020, 4 pages.
Ecoation, "A Fresh Climate Perspective: What is Stereo-Spatiotemporal Data Collection and Why is it Important," Oct. 15, 2020, 6 pages.
Ecoation, "Our Products / Ecoation Website," Oct. 27, 2020, 14 pages.
Priva, "Priva Sensors for horticulture," Oct. 2020, 5 pages.
SemiosBio Technologies Inc., "We Help Growers Worry Less," Oct. 2020, 8 pages.
Sencrop, "Connected ag-weather: learn more about stations," Oct. 2020, 7 pages.
Fuxman et al., "Real-Time Projections and Estimated Distributions of Agricultural Pests, Diseases, and Biocontrol Agents," U.S. Appl. No. 16/883,354, filed May 20, 2020, 52 pages.
Stewart et al., "Platform for Real-Time Identification and Resolution of Spatial Production Anomalies in Agriculture," U.S. Appl. No. 17/062,381, filed Nov. 13, 2020, 79 pages.
Fuxman et al., "Reduction of Time of Day Variations in Plant-Related Data Measurements," U.S. Appl. No. 17/062,397, filed Oct. 2, 2020, 72 pages.
Stewart et al., "System and Method for Testing Plant Genotype and Phenotype Expressions Under Varying Growing and Environmental Conditions," U.S. Appl. No. 17/062,407, filed Oct. 2, 2020, 75 pages.
Humpston et al., "Stereo-Spatio-Temporal Crop Condition Measurements for Plant Growth and Health Optimization," U.S. Appl. No. 17/098,144 filed on Nov. 13, 2020, 80 pages.
Humpston et al., "Generation on Stereo-Spatio-Temporal Crop Condition Measurements Based on Human Observations and Height Measurements ," U.S. Appl. No. 17/098,193 filed on Nov. 13, 2020, 80 pages.
Office Action dated Mar. 16, 2023 in connection with U.S. Appl. No. 17/098,144, 15 pages.
Final Office Action dated Aug. 3, 2023 in connection with U.S. Appl. No. 17/098,144, 13 pages.
Supplementary European Search Report dated Jun. 25, 2024 in connection with European Patent Application No. 21890426.6, 9 pages.

* cited by examiner

FIG. 9

DATA PROCESSING PLATFORM FOR ANALYZING STEREO-SPATIO-TEMPORAL CROP CONDITION MEASUREMENTS TO SUPPORT PLANT GROWTH AND HEALTH OPTIMIZATION

TECHNICAL FIELD

This disclosure is generally directed to plant monitoring and assessment. More specifically, this disclosure is directed to a data processing platform for analyzing stereo-spatio-temporal crop condition measurements to support plant growth and health optimization.

BACKGROUND

When plants are grown on a large scale, such as in protected cultivation (like a greenhouse) or outdoors, both the plants and their growers face various challenges. For example, production greenhouses can involve very complex and geographically large operations with varying environmental conditions. The management of growing operations in production greenhouses can be difficult and time consuming, and conventional approaches for managing the growing operations in greenhouses can suffer from a number of shortcomings. The same problems and difficulties can occur in other large growing areas, such as in open outdoor fields.

SUMMARY

This disclosure relates to a data processing platform for analyzing stereo-spatio-temporal crop condition measurements to support plant growth and health optimization.

In a first embodiment, an apparatus includes at least one processor configured to obtain stereo-spatio-temporal data measurements of plants in a growing area. The stereo-spatio-temporal data measurements include (i) first spatio-temporal data measurements of the plants in the growing area and (ii) second spatio-temporal data measurements of the plants in the growing area. The at least one processor is also configured to analyze the stereo-spatio-temporal data measurements to identify one or more actual or potential problems associated with one or more of the plants. The at least one processor is further configured to generate a graphical user interface identifying at least one of the one or more actual or potential problems with the one or more plants. The first and second spatio-temporal data measurements of each stereo-spatio-temporal data measurement are associated with at least one common plant characteristic and different three-dimensional positions within the growing area taken at one or more known times.

In a second embodiment, a method includes obtaining stereo-spatio-temporal data measurements of plants in a growing area. The stereo-spatio-temporal data measurements include (i) first spatio-temporal data measurements of the plants in the growing area and (ii) second spatio-temporal data measurements of the plants in the growing area. The method also includes analyzing the stereo-spatio-temporal data measurements to identify one or more actual or potential problems associated with one or more of the plants. The method further includes generating a graphical user interface identifying at least one of the one or more actual or potential problems with the one or more plants. The first and second spatio-temporal data measurements of each stereo-spatio-temporal data measurement are associated with at least one common plant characteristic and different three-dimensional positions within the growing area taken at one or more known times.

In a third embodiment, a non-transitory computer readable medium contains instructions that when executed cause at least one processor to obtain stereo-spatio-temporal data measurements of plants in a growing area. The stereo-spatio-temporal data measurements include (i) first spatio-temporal data measurements of the plants in the growing area and (ii) second spatio-temporal data measurements of the plants in the growing area. The medium also contains instructions that when executed cause the at least one processor to analyze the stereo-spatio-temporal data measurements to identify one or more actual or potential problems associated with one or more of the plants. The medium further contains instructions that when executed cause the at least one processor to generate a graphical user interface identifying at least one of the one or more actual or potential problems with the one or more plants. The first and second spatio-temporal data measurements of each stereo-spatio-temporal data measurement are associated with at least one common plant characteristic and different three-dimensional positions within the growing area taken at one or more known times.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which:

FIG. 9 illustrates a third example type of graphical user interface generated based on an analysis of stereo-spatio-temporal crop condition measurements for plant growth and health optimization according to this disclosure;

DETAILED DESCRIPTION

Figure 1:
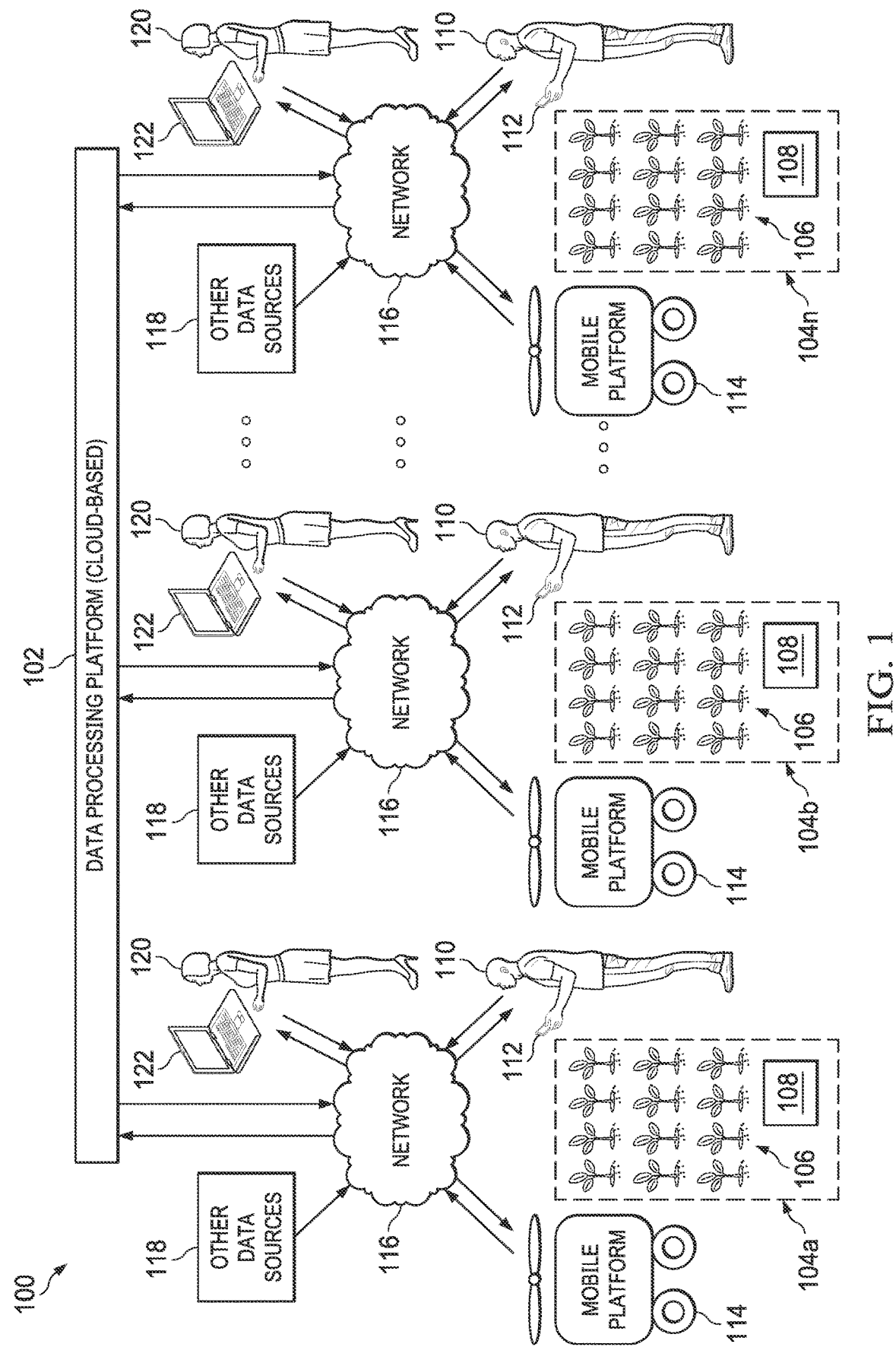
FIG. 1 illustrates an example system supporting stereo-spatio-temporal crop condition measurements and analyses for plant growth and health optimization according to this disclosure.

FIGS. 1 through 11, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, when plants are grown on a large scale, such as in protected cultivation (like a greenhouse) or outdoors, both the plants and their growers face various challenges. For example, production greenhouses can involve very complex and geographically large operations with varying environmental conditions.

The management of growing operations in production greenhouses can be difficult and time consuming, and conventional approaches for managing the growing operations in greenhouses can suffer from a number of shortcomings. The same problems and difficulties can occur in other large growing areas, such as in open outdoor fields.

As one example issue, plants need to be kept within a range of ideal conditions in order to increase or optimize their growth and health and thereby increase or optimize their yields of production items like fruits or vegetables. There are strong links between key environmental or climatic data (such as temperature, humidity, carbon dioxide level, and level of photosynthetically active radiation (PAR)) and plant growth and health, production yields, the prevalence of pests or diseases, and other traits that may or may not be desirable. During plant management, a number of plant-related variables are typically monitored, and various analyses can typically be performed. The analyses can be used to decide how best to optimize growing conditions in a complex multivariable environment. The analyses can also be used to identify actions (such as controlling climatic variables or deploying pesticides or other treatments) to be performed manually or in an automated manner. The overall goal here is to achieve a desired effect, such as optimal production yields with minimal resource usage and minimal pesticide usage. This cycle of sensing, analyzing, and acting can occur repeatedly to obtain an improved understanding of cause and effect in a growing area and to continuously improve further optimizations in the growing area.

Ideally, each plant in a growing area would be kept within a range of ideal conditions in terms of every metric of relevance. If each variable of importance could be sensed directly and perfectly controlled on a per-plant basis, this might be possible to achieve. However, imperfect sensing, imperfect control fidelity, and imperfect understanding of cause and effect are common in a large-scale growing area, so this becomes a very challenging multivariable control problem. A greater variety of sensed plant-related parameters and an increased fidelity of parameter measurements (such as though quantity and quality of information) can have a large impact on how operations are performed in a growing area.

Many monitoring systems today use a small number of fixed, simple environmental sensors that are placed periodically around a greenhouse or other growing area to capture climatic data over time. While temporal fidelity is good, this approach provides limited spatial fidelity horizontally (such as in the X and Y axes) and provides no high-fidelity information at all about how conditions change vertically (such as in the Z axis). One reason for this is that capturing this type of information would require the fixed sensors to be mounted in locations where the sensors would interfere with the performance of plant-related operations performed by humans or automated systems. Moreover, the fidelity of information has a generally liner relationship with the total cost of the sensors, meaning high-fidelity information is typically very costly to obtain. As a result, complex, expensive single sensors are not commercially viable. As a particular example, no commercial sensor system based on this approach incorporates hyperspectral cameras to date because of the high cost of obtaining and installing hyperspectral cameras at multiple locations throughout a growing area.

In one aspect, this disclosure provides a mobile platform for capturing stereo-spatio-temporal crop condition measurements. As described in more detail below, the mobile platform can be used to achieve increased fidelity in data collection, such as in terms of type, quantity, and quality of data collected. In another aspect, this disclosure provides a data processing platform for processing stereo-spatio-temporal crop condition measurements in order to identify operations to help optimize plant growth and health, which may thereby help to increase or maximize production yields. As described in more detail below, the data processing platform can process the increased-fidelity data, such as the data measurements that are captured by at least one mobile platform, which enables new and better analyses of plant-related data and ultimately greater optimization of selected desirable traits in plant growth operations. Note that the functionality described in this patent document may be used with various types of growing areas, such as commercial greenhouses, vertical farms, and open fields.

The mobile platform described below can include one or more plant-related sensors mounted to a lower portion of the mobile platform, and one or more additional plant-related sensors can be mounted to a movable portion or other portion of the mobile platform. The mobile platform may be driven by a human operator or moved in a controlled and automated manner around a growing area. The sensor(s) mounted to the lower portion of the mobile platform can be used to capture measurements in multiple dimensions of the growing area (such as in the X, Y, and Z dimensions), and the sensor(s) mounted to the movable or other portion of the mobile platform can be used to capture measurements in the multiple dimensions of the growing area (such as in the X, Y, and Z dimensions). In some cases, the sensor(s) mounted to the lower portion of the mobile platform can be used to capture measurements at a fixed height (a fixed position in the Z dimension), while the sensor(s) mounted to the movable or other portion of the mobile platform can be used to capture measurements at a different fixed height or a variable height (a fixed or variable position in the Z dimension). Additionally, measurements may be captured at the same or similar locations (such as the same or similar X-Y-Z locations) of the growing area over time, which may provide an additional dimension (a time or T dimension) to the measurements. The frequency of measurement at any given location may be singular, intermittent/irregular, or periodic as needed or desired. The data processing platform can receive and process these measurements (possibly along with other data) in order to perform one or more plant-related analyses and perform one or more other plant-related functions. Note that X, Y, Z, and T are used here merely to describe how measurements can be captured along various axes or dimensions of a growing area over time, but this does not impart any particular limitations on the layout or arrangement of the growing area or on the timing or other operation of a mobile platform. Also note that, in some cases, the measurements forming each stereo-spatial-temporal data measurement may represent measurements captured at different XYZ positions (where at least one of X, Y, and Z is different) captured at or substantially near the same time (or otherwise close enough so that the data measurements can be viewed as being related).

Instead of or in addition to the sensors of the mobile platform, at least some spatio-temporal data may be gathered by the mobile platform from at least one human operator or other personnel. For example, the mobile platform may include a touchscreen or other input mechanism(s) that allow a human operator to interface with the mobile platform and manually provide data measurements to the mobile platform. A positioning system of the mobile platform or an external positioning system can identify the position of the mobile platform in a growing area in at least two dimensions (such as the X and Y dimensions), and a height sensor of the mobile platform may measure how high the movable portion of the mobile platform has been raised. The mobile platform may then tag the data measurements provided by the human operator, such as with XYZ position and time information, to generate stereo-spatial-temporal data measurements. In this way, even manually-provided stereo-spatial-temporal data can be obtained and processed in order to gain certain insights into plant conditions. As a particular example, this may allow a human scout to identify a pest or disease on the roots of a plant and indicate that the pest/disease is of limited extent and does not affect the middle or top of the plant. The data processing platform can use this information to recommend a suitable treatment, such as a treatment that might not have been recommended if the pest/disease was affecting the middle or top of the plant.

The mobile platform can be used to capture measurement data at different locations of at least one growing area and at different times of day, season, or growing cycle. In this way, the mobile platform can be used to capture a large amount of spatio-temporal data. Moreover, by mounting the same types of sensors to the lower and movable or other portions of the mobile platform or otherwise capturing data at multiple heights, the mobile platform can be used to capture stereo-spatio-temporal measurement data, which allows differences between the spatio-temporal data at different heights of monitored plants to be identified and used by the mobile platform or the data processing platform. This approach therefore provides a cost-effective mechanism for measuring numerous (and possibly all) relevant portions of a greenhouse or other growing area over time, which may provide a massive increase in the fidelity of data that is available for processing. Also, this approach allows a limited number of more expensive sensors to be used to collect data about plants in a growing area, which makes the use of newer or more-expensive sensors commercially viable and further increases the fidelity of data.

The increased quantity and quality of data also improves the data analyses that can be performed by the data processing platform and enables new analyses to be performed by the data processing platform. This may allow, for example, improvements in the plant-growing or plant-treating recommendations that are produced by the data processing platform. Any recommendations identified by the data processing platform may be provided to humans for the implementation of appropriate interventions or used to provide automated interventions (which may or may not require human approval). Depending on the implementation, the interventions may represent improved optimizations of actions already recommended by existing monitoring systems, or the interventions may represent new interventions that are not possible given the limitations of existing systems. Ultimately, this can lead to increased optimizations for desired outcomes, such as improved plant growth and health, improved production yields, or reduced pests/diseases (which can translate into increased revenues and increased profit margins).

In the following discussion, sensors of the mobile platform and the data processing platform may be used to capture and process any suitable plant-related measurement data associated with plants being grown and monitored in one or more greenhouses or other growing areas. In some cases, the measurement data may include plant production data, physical plant data, climate data, pest and disease data, crop work data, and crop treatment data. Note that one, some, or all of these types of data measurements may be captured and used. Also, note that any other or additional type(s) of plant-related data measurements may be captured by the mobile platform and processed by the data processing platform.

Plant production data generally refers to data identifying one or more physical characteristics associated with actual production by plants being monitored in at least one greenhouse or other growing area. Fruits, vegetables, ornamental flowers, or other production produced by plants may be generally referred to as "production items," and any characteristics of the production items may be generally referred to as "production characteristics." Examples of plant production data may include a number of production items currently growing on plants; a number of production items on the ground or removed from plants; one or more colors of production items; a taste of production items; a shine of production items; a firmness of production items; a shape of production items; a smell of production items; internodal distance between production item-bearing branches of plants; a leaf area index of leaves of plants; a size of foliage of plants; a color of foliage of plants; a thickness of foliage of plants; a distribution of flowers of plants; a number of flowers of plants; total harvest (such as weight per row of plants) for a particular time period; and/or yield assessment (such as sizes and weights of fruits, vegetables, ornamental flowers, or other harvested production). In some cases, the colors of fruits, vegetables, ornamental flowers, or other production items may be used as indicators of ripeness or ready states of the production. These example types of plant production data are for illustration only.

Physical plant data generally refers to data identifying one or more physical characteristics associated with plants being monitored in at least one greenhouse or other growing area. Examples of physical plant data may include heights of plants; widths of plants; visual data (such as one or more colors) associated with plants' leaves, stems, or other portions; spectrographic data associated with plants' leaves, stems, or other portions; a number of plant stems growing in each of various locations; a spacing of plant stems growing in each of various locations; a density of plant stems at each of various locations; thicknesses of plant stems; an amount of water provided to each plant; one or more nutrients provided to each plant; the phenotype of each plant; the smell of each plant associated with its chemical composition and nutritional value and taste; and/or the color of fruits and foliage associated with stress levels and health of the plants. These example types of physical plant data are for illustration only.

Climate data generally refers to data identifying climatic conditions of plants being monitored in at least one greenhouse or other growing area. Examples of climate data may include temperature; absolute or relative humidity; wind/air speed; carbon dioxide level; oxygen level; nitrogen dioxide level; ethylene level; amount of natural or artificial light; flux of PAR, PYR, or any other selected spectral weighting of light from the top of the canopy to the bottom of the canopy for the plants; spectral composition of light from the top of the canopy to the bottom of the canopy for the plants; vapor-pressure deficit (VPD); dew point; and/or thermal imaging. Since climatic conditions can often vary even within the same greenhouse, field, or other growing area, at least some of the climate data can be specific to each individual plant being monitored. These example types of climate data are for illustration only.

Pest and disease data generally refers to data identifying pests or diseases that might be affecting plants being monitored in at least one greenhouse or other growing area. Pests refer to animals or plants that are detrimental to the growth or well-being of plants being monitored. Pests can include ectoparasites such as certain types of insects, mites, and vertebrates. Specific examples of pests can include whiteflies, aphids, thrips, spider mites, russet mites, mealybugs, caterpillars, sciarid flies, shore flies, leaf miners, vine weevils, red palm weevils, white grubs, and loopers. Diseases refer to pathogens that are detrimental to the growth or well-being of plants being monitored. Specific examples of diseases may include certain types of bacteria, viruses, fungi like powdery mildew, oomycetes, protozoa, and nematodes. Examples of pest and disease data may include a number or quantity of each pest or disease at each of various locations; a current pressure of each pest or disease at each of various locations; historical data regarding pests and diseases; and/or human, machine, or plant movements that may represent vectors for spreading pests and diseases. These example types of pest and disease data are for illustration only.

Crop work data generally refers to data identifying one or more characteristics associated with how humans or machines manipulate, modify, and (possibly) damage plants being monitored in at least one greenhouse or other growing area. Examples of crop work data may include a number of plants remaining after plant work has been completed; a number of stems remaining after plant work has been completed; a spacing of plants or stems after plant work has been completed; a number of broken plant heads present after plant work has been completed; whether deleafing was performed during plant work; and/or a number of leaves or other portions of plants on the ground or removed as a result of plant work. These example types of crop work data are for illustration only.

Crop treatment data generally refers to data identifying one or more treatments, interventions, or biocontrol agents (collectively referred to as "treatments") that are used to help combat pests, diseases, or other problems with plants being monitored in at least one greenhouse or other growing area. Treatments can include the application or use of beneficial organisms, insecticidal soaps (such as one containing a potassium salt of fatty acids), fertilizers, chemical insecticides, herbicides, or other chemical treatments. Beneficial organisms generally include living organisms that are beneficial to the growth or well-being of plants being monitored, such as organisms that attack or reduce pests or diseases. Specific examples of beneficial organisms may include certain types of parasitic wasps, predatory mites, beetles (such as ladybugs and ladybirds), fungi, and nematodes. Examples of crop treatment data may include an identification of the treatment(s) applied, a quantity of each treatment applied, and a date/time when each treatment was applied. These example types of crop treatment data are for illustration only.

In the discussion above and in the discussion below, it is often assumed that part of the mobile platform is movable up and down in the height dimension. It is also often assumed that spatio-temporal data measurements are captured at different heights of plants and that analyses of stereo-spatio-temporal data measurements are based on differences along the heights of plants. However, it is also or alternatively possible to capture stereo-spatio-temporal data measurements along other dimensions, such as across the width or depth of plants, and to analyze those stereo-spatio-temporal data measurements. As a result, this disclosure is not limited to capturing spatio-temporal data measurements at different heights or analyzing stereo-spatio-temporal data measurements based on differences in measurements along the heights of plants.

FIG. 1 illustrates an example system 100 supporting stereo-spatio-temporal crop condition measurements and analyses for plant growth and health optimization according to this disclosure. As shown in FIG. 1, the system 100 includes at least one data processing platform 102, which may be used in conjunction with one or more growing areas 104a-104n. The data processing platform 102 collects and processes data (including stereo-spatio-temporal crop condition measurements) associated with various plants 106 being grown in the one or more growing areas 104a-104n. The plants 106 represent any suitable plants being grown and whose condition is monitored and assessed, and the plants 106 may be used for any suitable purposes. For example, the plants 106 may represent crops that provide food for people or animals, crops that provide material for industrial or medicinal purposes, or flowers or other ornamental plants. In general, the system 100 may be used to monitor and assess any suitable type(s) of plant(s) 106, including a single type of plant 106 or multiple types of plants 106. The system 100 may also be used to monitor and assess any suitable number of plants 106.

Each growing area 104a-104n represents any suitable space in which plants 106 can be grown, monitored, and assessed. For example, in some embodiments, each growing area 104a-104n may represent a greenhouse or other protected cultivation area or a portion thereof. Protected cultivation technology is generally used to provide favorable climatic conditions for one or more specific types of plants 106, which can vary based on the specific plants 106 being grown. These favorable climatic conditions can reduce stress levels on the plants 106 and help increase production yields obtained from the plants 106. In other embodiments, each growing area 104a-104n may represent an open field or other outdoor or unprotected area or a portion thereof. In general, the system 100 may be used to monitor and assess plants 106 in any suitable type(s) of growing area(s) 104a-104n, including a single type of growing area 104a-104n or multiple types of growing areas 104a-104n. The system 100 may also be used to monitor and assess plants 106 in any suitable number of growing areas 104a-104n.

Each growing area 104a-104n may optionally include one or more types of equipment 108 used to help facilitate growth of the plants 106. For example, each growing area 104a-104n may include irrigation equipment configured to provide water to the plants 106 and, if necessary, drainage equipment configured to handle water that is not retained by the plants 106 or their associated containers (if any). Each growing area 104a-104n may also include nutrition equipment configured to provide nutritional materials to the plants 106. At least part of the nutrition equipment might be integrated into or with the irrigation equipment so that at least some of the nutritional materials can be provided to the plants 106 via the water that is provided to the plants 106. Each growing area 104a-104n may further include lighting equipment configured to provide artificial lighting or to control natural lighting provided to the plants 106. Each growing area 104a-104n may also include temperature equipment configured to create a desired temperature or temperature range around the plants 106. Each growing area 104a-104n may further include humidity equipment configured to create a desired humidity or humidity range around the plants 106. Each growing area 104a-104n may also include carbon dioxide ($CO_2$) equipment configured to create a desired $CO_2$ level or $CO_2$ range around the plants 106. In addition, each growing area 104a-104n may include pruning, spraying, and/or harvesting equipment used to physically prune the plants 106, spray insecticide or other materials onto the plants 106, and/or harvest the plants 106 or portions thereof In general, the system 100 may use any suitable type(s) of equipment 108 in each growing area 104a-104n to perform any desired operation(s) involving the plants 106. Note that the specific equipment 108 used here can vary based on a number of factors, such as based on the specific types of plants 106 and whether the plants 106 are grown indoors or outdoors. Also, note that different growing areas 104a-104n can include the same type(s) of equipment 108 or different types of equipment 108.

In many cases, the plants 106 in the one or more growing areas 104a-104n are arranged in a specified pattern. For example, the plants 106 in each growing area 104a-104n may typically be arranged in long rows of plants 106, where the rows are spaced apart from one another. This helps to provide space for people or objects to move between the plants 106 and to ensure that each plant 106 receives adequate lighting, air flow, moisture, etc. If used in a greenhouse, for example, each plant 106 or group of plants 106 may be placed into a suitable container, and the containers may be arranged in rows in order to facilitate easy movement of the plants 106 as needed or desired. In some instances, the containers themselves may be raised off the ground using suitable holders, which may help to facilitate improved drainage of the containers or to reduce the ability of pests to easily reach the containers. Greenhouses or other structures also often include vertical posts (possibly at generally regular intervals) that are used to provide structural support, and the posts may often be numbered or otherwise identified in order to identify specific locations in the greenhouses or other structures. For instance, plant positions or locations may be identified based on the plants' row numbers and post numbers.

One or more human scouts 110 are often employed to walk or ride around the one or more growing areas 104a-104n and to manually inspect the plants 106. For example, each human scout 110 may visually inspect various plants 106 in order to identify any fruits, vegetables, ornamental flowers, or other production items (or characteristics thereof) currently growing on the plants 106. Each human scout 110 may also visually inspect various plants 106 in order to identify any visible signs of pests, diseases, over- or under-watering, malnutrition, or other problems (or characteristics thereof) associated with the plants 106. As another example, each human scout 110 may visually inspect various plants 106 in order to identify any beneficial organisms (or characteristics thereof) present on or near the plants 106. As yet another example, each human scout 110 may carry one or more instruments that can be used to perform instrument-based inspections of the plants 106.

In this example, each human scout 110 may carry or otherwise have access to a tablet computer or other mobile electronic device 112, which the human scout 110 may use to provide or retrieve data. For example, each human scout 110 may use a mobile electronic device 112 to capture still, video, or thermal images of plants 106 being inspected, identify any fruits/vegetables/flowers/other production items associated with the plants 106 being inspected, identify any pests/diseases/other conditions associated with the plants 106 being inspected, or identify any beneficial organisms associated with the plants 106 being inspected. Each human scout 110 may also use a mobile electronic device 112 to enter the specific location or locations (such as the heights) where one or more plants 106 may be suffering from one or more problems, where one or more production items or beneficial organisms are located, or where one or more other characteristics of the plants 106 are noted by the human scout 110. Note that the mobile electronic device 112 may be a handheld device or may be incorporated into a larger mobile device, such as a mobile platform as described below. Also, note that still, video, or thermal images of plants 106 may be captured in any suitable manner, such as standard two-dimensional (2D) imaging, 360° imaging, or stereoscopic three-dimensional (3D) imaging (which may be created with either 2D plus depth information or a combination of left and right video information).

Each mobile electronic device 112 may also identify its location in order to associate captured information or to provide useful information related to one or more plants 106 at or near its location. For example, a mobile electronic device 112 may identify its X-Y location or other location and associate any information input by a human scout 110 or any information captured by one or more sensors with that location. This may allow, for instance, the mobile electronic device 112 to automatically associate information input by the human scout 110 or captured by one or more sensors with that location or with one or more plants 106 at or near that location. As another example, a mobile electronic device 112 may identify its location and output to a human scout 110 any pests or diseases previously identified at or near its location or any pests or diseases projected to now exist at or near its location. Note, however, that in other embodiments the identification of the location of a mobile electronic device 112 may occur in another component external to the mobile electronic device 112, in which case the external component may be responsible for associating captured information with the mobile electronic device's location or for providing information based on the mobile electronic device's location.

Any suitable technique may be used to identify a location of each mobile electronic device 112, such as manual input from a user, the use of Global Positioning System (GPS) or Ultra-Wideband (UWB) positioning, visual odometry, the scanning of optical tags (such as bar codes or QR codes), or the transmission or receipt of radio frequency identification (RFID) signals or other wireless signals. Note that this disclosure is not limited to any particular location identification technique. The specific location identification technique(s) used in the system 100 can vary as needed or desired, and a location identification technique may be used within or external to the mobile electronic devices 112. Also, a determined location may be expressed in any suitable manner, such as row/post numbers, GPS coordinates, or other expression of location.

One or more mobile platforms 114 (also referred to as robotic platforms 114) may also be employed to move around the one or more growing areas 104a-104n and to automatically inspect the plants 106. For example, each mobile platform 114 may include one or more cameras for capturing still, video, or thermal images of plants 106 being inspected. Each mobile platform 114 also includes multiple sensors for measuring one or more aspects associated with the plants 106 being inspected or other components configured to collect measurement data associated with the plants 106 being inspected. Again, still, video, or thermal images of plants 106 may be captured in any suitable manner, such as standard 2D imaging, 360° imaging, or stereoscopic 3D imaging. Each mobile platform 114 may include any suitable type(s) of sensors or other measurement devices, such as physiological sensors, surface analysis sensors, chemical sensors, thermal sensors, microclimate sensors, image-based or video-based sensors, spectroscopy sensors (including multispectral and hyperspectral sensors), volatile organic compound sensors, or canopy scanning sensors. Note that the same type(s) of sensors may also or alternatively be used by the human scouts 110 or other electronic devices 112 used by the human scouts 110, or the human scouts 110 and mobile platforms 114 may use different types of sensors.

Each mobile platform 114 may also identify its location or engage in actions that allow an external component to identify its location. Any suitable technique may be used by each mobile platform 114 or another component to identify a location of the mobile platform 114, and determined locations may be expressed in any suitable manner. Example techniques may include the use of GPS or UWB positioning, visual odometry, the scanning of optical tags (such as bar codes or QR codes), or the transmission or receipt of RFID signals or other signals. Again, note that this disclosure is not limited to any particular location identification technique(s), and a location identification technique may be used within or external to each mobile platform 114.

Any suitable type(s) of mobile platform(s) 114 may be used in the system 100 to automatically inspect plants 106 in one or more growing areas 104a-104n. Examples of the mobile platform 114 are described in further detail below. In other embodiments, devices as provided in U.S. Pat. No. 10,241,097; U.S. Patent Application Publication No. 2017/0032258; and U.S. patent application Ser. No. 16/990,212 (all of which are hereby incorporated by reference in their entirety) may be modified in accordance with the teachings of this disclosure and used here. In still other embodiments, the IRIS SCOUT ROBOT robotic scout from ECOATION INNOVATIVE SOLUTIONS INC. may be modified in accordance with the teachings of this disclosure and used here. Note, however, that this disclosure is not limited to use with any particular type of mobile platform 114.

At least one network 116 may be used to facilitate communications between various components of the system 100. For example, the network 116 may communicate using Internet Protocol (IP) packets, frame relay frames, Asynchronous Transfer Mode (ATM) cells, or other suitable methods between network addresses. The network 116 may include one or more local area networks (LANs), metropolitan area networks (MANs), wide area networks (WANs), all or a portion of a global network such as the Internet, or any other communication system or systems at one or more locations. The network 116 may also operate according to any appropriate communication protocol or protocols. The network 116 may include one or more public networks and/or one or more private networks. In some cases, the network 116 may include at least one wireless network that facilitates wireless communications with the mobile electronic devices 112 and the mobile platforms 114, as well as at least one wired network that facilitates wired communications. Note that the network 116 may or may not represent a network associated exclusively with one or more individual growing areas 104a-104n. As a particular example, the network 116 may represent a 5G network that can provide mobile data communication services over a specified area that includes at least one growing area 104a-104n.

In some cases, one or more other data sources 118 may be provided for a growing area. The one or more other data sources 118 represent data sources separate from the human scouts 110 and mobile platforms 114. These other data sources 118 may represent any other suitable source(s) of data related to the growing of the plants 106. For example, the other data sources 118 may include one or more fixed sensors located at one or more points in or around the one or more growing areas 104a-104n. These fixed sensors may be used to collect any suitable information, such as natural or artificial lighting conditions, humidity, or other conditions that affect multiple plants 106 or multiple growing areas 104a-104n. As a particular example, the other data sources 118 may include fixed "climate boxes" that include various sensors for measuring climatic conditions, where the climate boxes are positioned every few acres in a growing area. The other data sources 118 may also or alternatively include external sources of information, such as predicted near-term weather or predicted long-term climate conditions.

Note that while all growing areas 104a-104n are shown here as having a common layout, each growing area 104a-104n may include all or a subset of the illustrated components in any suitable arrangement. Also, note that the growing areas 104a-104n may have common or different arrangements. Thus, for example, one or some of the growing areas 104a-104n may use only human scouts 110 with electronic devices 112, one or some of the growing areas 104a-104n may use only mobile platforms 114, and one or some of the growing areas 104a-104n may use a combination of human scouts 110 and mobile platforms 114. As another example, each of the growing areas 104a-104n may or may not include or be associated with one or more other data sources 118. In general, each of the growing areas 104a-104n may include at least one source of plant-related data for the plants 106 in that growing area (whether human, robotic, or other).

The data processing platform 102 is communicatively coupled to the network 116 and is configured to process data collected or provided by the mobile electronic devices 112, the mobile platforms 114, and/or the other data sources 118. The data processing platform 102 can also interact with the mobile electronic devices 112 and the mobile platforms 114, such as by providing data to the mobile electronic devices 112 for use by the human scouts 110 and by providing data to the mobile platforms 114 to control scouting.

As described in more detail below, each mobile platform 114 includes one or more sensors mounted to a lower portion of the mobile platform 114 and one or more sensors mounted to a movable or other portion of the mobile platform 114. The sensor(s) mounted to the lower portion of the mobile platform 114 can be used to capture spatio-temporal measurement data in multiple dimensions of a growing area 104*a*-104*n*, and the sensor(s) mounted to the movable or other portion of the mobile platform 114 can be used to capture spatio-temporal measurement data in the multiple dimensions of the growing area 104*a*-104*n*. As noted above, in some cases, the sensor(s) mounted to the lower portion of the mobile platform 114 can be used to capture measurements at a fixed height, while the sensor(s) mounted to the movable or other portion of the mobile platform 114 can be used to capture measurements at a fixed or variable height. Additionally, measurements may be captured at the same or similar locations (such as the same or similar X-Y-Z locations) of a growing area 104*a*-104*n* over time, which may provide an additional time dimension T to the measurements. Note that each mobile platform 114 may be driven or otherwise controlled by a human operator, such as by a human scout 110, or controlled in an automated manner, such as by the data processing platform 102. Also or alternatively, the mobile platform 114 may include a touch-screen or other input mechanism(s) allowing manual input of data measurements to the mobile platform 114 by a human operator, and a positioning system and a height sensor of the mobile platform 114 may be used to tag or associate X-Y-Z locations or other locations and times with the manually-provided data measurements to produce stereo-spatio-temporal measurement data.

Also, as described in more detail below, the data processing platform 102 can receive and process spatio-temporal measurement data (possibly along with other data) in order to perform one or more plant-related analyses and perform one or more other plant-related functions. For example, the data processing platform 102 may identify differences in spatio-temporal measurement data by height or other dimension(s) of various plants 106 and make intervention recommendations or trigger interventions based on the analyses. As part of the processing, the data processing platform 102 may generate one or more graphical user interfaces for use by users (such as the human scouts 110) based on the spatio-temporal measurement data.

Figure 6:
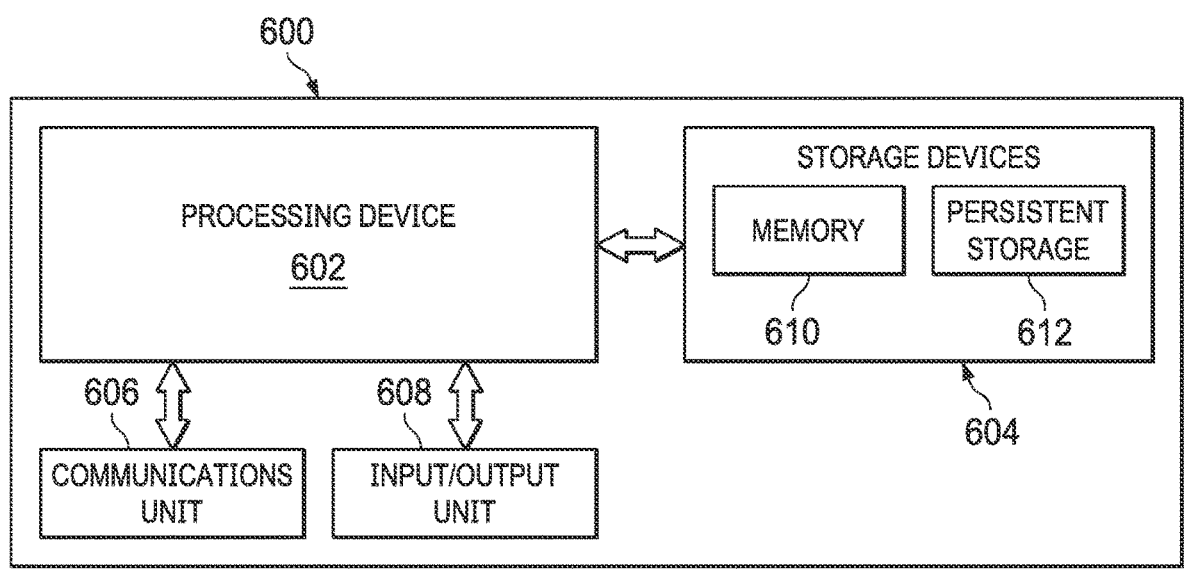
FIG. 6 illustrates an example device supporting analyses of stereo-spatio-temporal crop condition measurements for plant growth and health optimization according to this disclosure.

The data processing platform 102 includes any suitable structure configured to process plant-related data and to perform one or more functions using the plant-related data. For example, the data processing platform 102 may represent at least one desktop computer, laptop computer, server computer, or other computing device. The data processing platform 102 may be local to or remote from the one or more growing areas 104*a*-104*n*. In some cases, for instance, the data processing platform 102 may be implemented in a cloud-based environment or using one or more remote servers. Among other things, this may allow a service provider to provide its data processing capabilities to a number of growers over a small or wide geographic area. This may also allow a service provider to collect a large amount of data related to a large number of plants 106 being grown, which the service provider may then process in order to perform various functions. However, the data processing platform 102 may be implemented in any other suitable manner. One example of the data processing platform 102 is shown in FIG. 6, which is described below.

In some cases, the data processing platform 102 may communicate with one or more additional users 120 in one or more of the growing areas 104*a*-104*n*. The one or more additional users 120 may use one or more electronic devices 122. The additional users 120 may represent any suitable users associated with the plants 106 or the growing areas 104*a*-104*n*, such as one or more experts, non-experts, growers, or crop-site managers. The electronic devices 122 may represent any suitable electronic devices for interacting with the data processing platform 102, such as desktop computers, laptop computers, tablet computers, or mobile smartphones. The users 120 and their electronic devices 122 may be located local to or remote from the one or more growing areas 104*a*-104*n*.

Although FIG. 1 illustrates one example of a system 100 supporting stereo-spatio-temporal crop condition measurements and analyses for plant growth and health optimization, various changes may be made to FIG. 1. For example, the system 100 may include any suitable number of plants 106 in any suitable number of growing areas 104*a*-104*n*, and the plants 106 may be inspected by any suitable number of human scouts 110 and/or mobile platforms 114. Also, the system 100 may include any suitable number of data processing platforms 102, and components such as networks 116 and other data sources 118 may or may not be shared across multiple growing areas 104*a*-104*n*. Further, each growing area 104*a*-104*n* may be associated with any suitable number of human scouts 110, electronic devices 112, mobile platforms 114, networks 116, and other data sources 118 (including none of one or more of these components). In addition, the system 100 may interact with any suitable number of additional users 120 in one or more of the growing areas 104*a*-104*n*.

Figure 2:
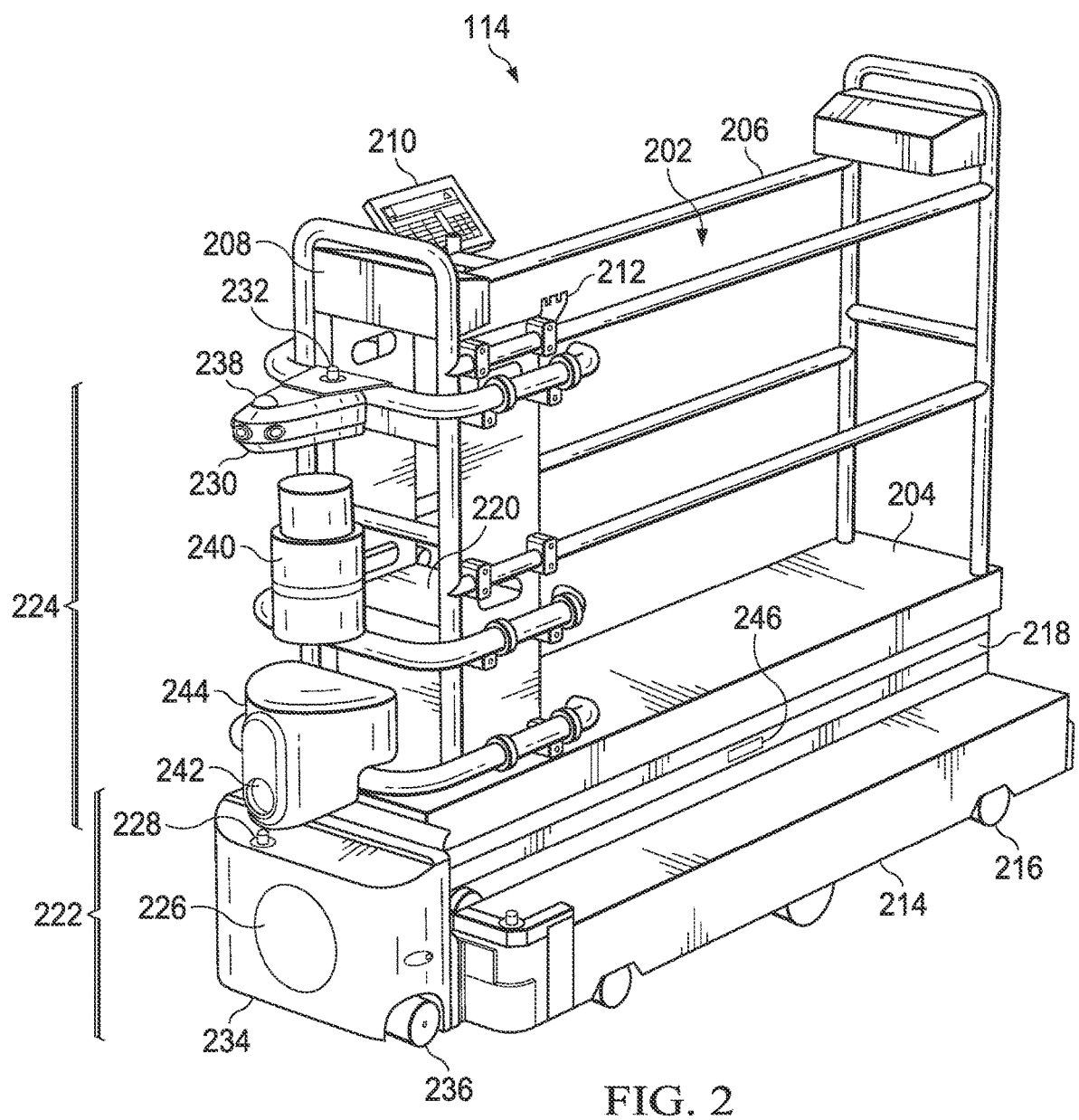
FIGS. 2 and 3 illustrate an example mobile platform supporting stereo-spatio-temporal crop condition measurements for plant growth and health optimization according to this disclosure.
Figure 3:
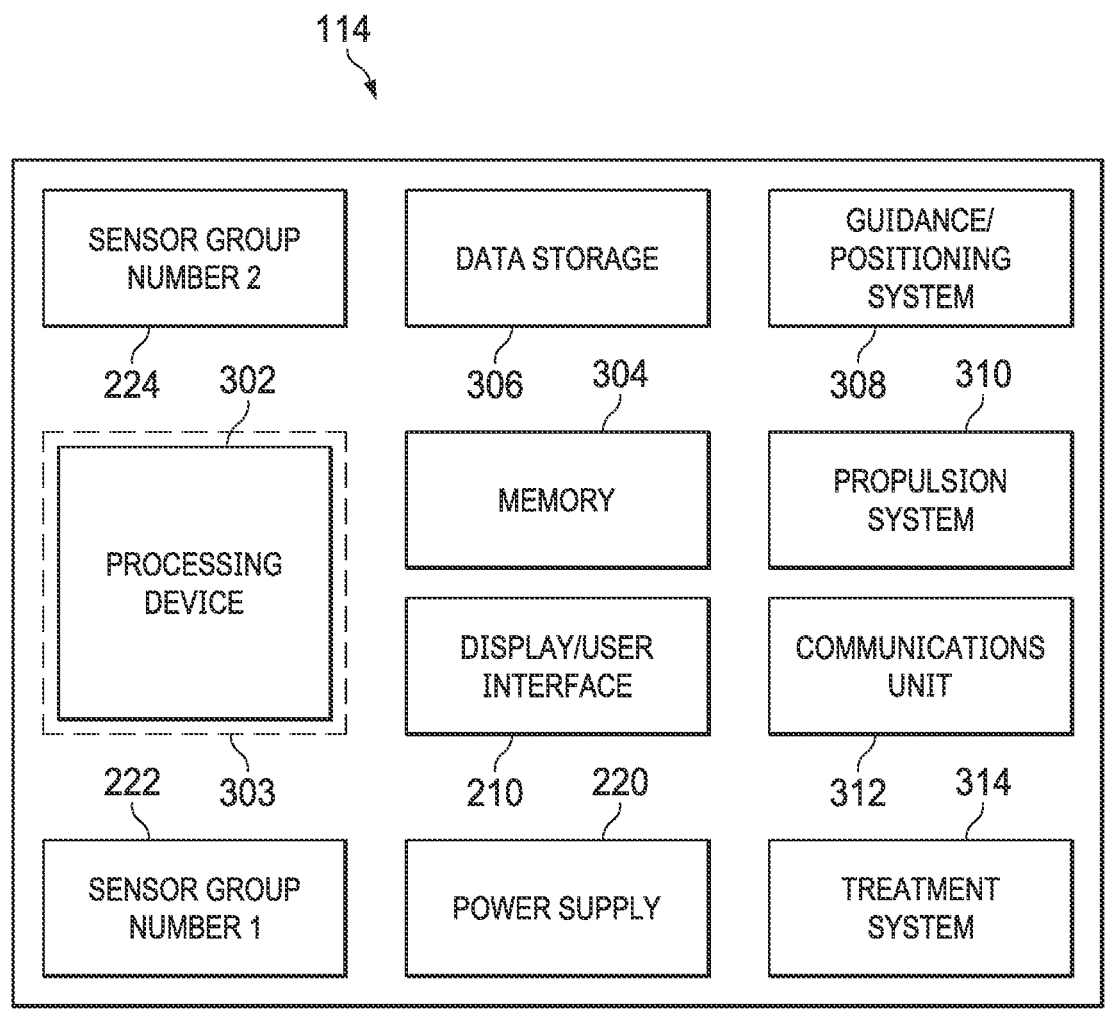

FIGS. 2 and 3 illustrate an example mobile platform 114 supporting stereo-spatio-temporal crop condition measurements for plant growth and health optimization according to this disclosure. For ease of explanation, the mobile platform 114 shown in FIGS. 2 and 3 is described as being used in the system 100 shown in FIG. 1. However, the mobile platform 114 may be used in any suitable system(s) and with any suitable growing area(s).

As shown in FIG. 2, the mobile platform 114 here is generally designed to carry and be driven by a human operator, such as a human scout 110. The mobile platform 114 defines a space 202 in which the human operator can stand in order to drive the mobile platform 114. The space 202 is defined by a platform 204 on which the human operator can stand and optionally by rails 206 that enclose the space 202. At least one of the rails 206 may be movable or removable in order to facilitate entry into and exit from the space 202 by the human operator. The space 202 may have any suitable size, shape, and dimensions. The platform 204 may be formed from any suitable material(s), such as one or more metals, and in any suitable manner. Also, the platform 204 may have any suitable size, shape, and dimensions. Each rail 206 may be formed from any suitable material(s), such as one or more metals, and in any suitable manner. In addition, each rail 206 may have any suitable size, shape, and dimensions.

A control panel 208 is provided on the mobile platform 114 to allow the human operator to control movement or other operations of the mobile platform 114. For example, the control panel 208 may allow the human operator to drive the mobile platform 114 forward and backward and to turn the mobile platform 114 left and right as desired. The control panel 208 may also allow the human operator to raise and lower or otherwise move a portion of the mobile platform 114 as described in more detail below. The control panel 208 may further allow the human operator to activate or control operations of various sensors or other components of the mobile platform 114. The control panel 208 includes any suitable controls for controlling any suitable operations of the mobile platform 114.

The mobile platform 114 can be used in conjunction with a mobile electronic device 210, which may be used to interface the human operator with the mobile platform 114, the data processing platform 102, or other system components. For example, the mobile electronic device 210 can display various plant-related information to or receive various plant-related information from the human operator. As particular examples, the mobile electronic device 210 may represent the mobile electronic device 112 described above, which can be used to capture still, video, or thermal images of plants 106 being inspected, identify any fruits/vegetables/flowers/other production items associated with the plants 106 being inspected and their heights/locations, identify any pests/diseases/other conditions associated with the plants 106 being inspected and their heights/locations, or identify any beneficial organisms associated with the plants 106 being inspected and their heights/locations. The mobile electronic device 210 may also receive one or more graphical user interfaces or other information from the data processing platform 102 for display to the human operator. The one or more graphical user interfaces may, for instance, graphically illustrate to the human operator where problems have been identified in plants 106 or where the human operator should perform one or more actions.

In addition, the mobile electronic device 210 may provide feedback or instructions to the human operator based on, for instance, analysis of data collected by sensors of the mobile platform 114 or wider datasets available within the system. As a particular example, the mobile electronic device 210 may present an instruction to drive the mobile platform 114 more slowly in a given area so that higher-fidelity temporal data may be collected by sensors of the mobile platform 114. As another particular example, the mobile electronic device 210 may provide feedback or instructions to the human operator of the mobile platform 114 from other humans using other elements of the system elsewhere, such as by providing instructions for the human operation to move the mobile platform 114 to specific locations in a greenhouse or other growing area to collect additional data.

The mobile electronic device 210 represents any suitable electronic device that can interact with a user. For instance, the mobile electronic device 210 may include a liquid crystal display (LCD), light-emitting diode (LED) display, or other display, which may optionally function as a touchscreen. The mobile electronic device 210 may also act as a communication portal that allows the human operator to interact with the mobile platform 114 or the data processing platform 102. The mobile electronic device 210 can be removable here so that the human operator can attach the mobile electronic device 210 to and remove the mobile electronic device 210 from the mobile platform 114 at one or more locations. This may allow, for example, the human operator to remove the mobile electronic device 210 while performing one or more plant-related actions or other actions.

Multiple mounting structures 212 may optionally be provided on the mobile platform 114, where each mounting structure 212 can receive and hold the mobile electronic device 210 in place. Each mounting structure 212 may also optionally provide power to the mobile electronic device 210 and/or provide a physical interface for communicating with other components of the mobile platform 114. Each mounting structure 212 represents any suitable structure configured to receive and retain a mobile electronic device 210. Note that while two mounting structures 212 are shown here, the mobile platform 114 may include any suitable number of mounting structures 212 (including a single mounting structure 212) in any suitable location(s), and each mounting structure 212 may be fixed or movable.

A base 214 of the mobile platform 114 represents or forms a part of a lower portion of the mobile platform 114 on or to which other components of the mobile platform 114 are attached or mounted. Among other things, the base 214 is attached to a propulsion system that controls various wheels 216, which can be used to move the base 214 and thereby move the mobile platform 114. The base 214 is also coupled to a lift 218, which can be used to selective raise and lower the platform 204 and various components coupled directly or indirectly to the platform 204. The lift 218 represents any suitable structure configured to raise and lower a movable portion of the mobile platform 114, such as a scissor lift.

A power supply 220 provides electrical power to various components of the mobile platform 114. The power supply 220 represents any suitable source of electrical power, such as one or more rechargeable batteries. The power supply 220 may also include a power management system that is configured to provide for switching between multiple energy sources or that incorporates safety and protection devices.

The mobile platform 114 also includes multiple sensor groups 222 and 224, which are mounted to different portions of the mobile platform 114. More specifically, the sensor group 222 is mounted directly or indirectly to the base 214 of the mobile platform 114, so the sensor group 222 is mounted to the lower portion or otherwise mounted at a lower position (height) of the mobile platform 114. The sensor group 224 is mounted directly or indirectly to the platform 204 of the mobile platform 114, so the sensor group 224 is mounted to the movable portion or otherwise mounted at a higher position (height) of the mobile platform 114. Among other things, the sensor group 222 includes one or more sensors that can be used to measure one or more plant-related characteristics of plants 106 at or near the bottoms of the plants 106, and the sensor group 224 includes one or more sensors that can be used to measure one or more plant-related characteristics of plants 106 at one or more higher locations of the plants 106. As noted above, however, the sensor groups 222 and 224 may also or alternatively be offset in other directions.

The sensor groups 222 and 224 include at least one common type of sensor in each group. For example, the sensor group 222 may include one or more lower canopy climate sensors 226 and a lower canopy light sensor 228, and the sensor group 224 may include one or more upper canopy climate sensors 230 and an upper canopy light sensor 232. The one or more lower canopy climate sensors 226 can be used to measure one or more plant-related climatic characteristics or other characteristics of the lower canopies or other lower portions of plants 106. The one or more upper canopy climate sensors 230 can be used to measure one or more plant-related climatic characteristics or other characteristics of the mid or upper canopies or other higher portions of plants 106. The lower canopy light sensor 228 can be used to measure one or more plant-related lighting characteristics, such as PAR light level, at the lower canopies or other lower portions of plants 106. The upper canopy light sensor 232 can be used to measure one or more plant-related lighting characteristics, such as PAR light level, at the mid or upper canopies or other higher portions of plants 106.

In some embodiments, the one or more lower canopy climate sensors 226 and the lower canopy light sensor 228 may generally remain fixed to capture measurements at or near the bottom of the height axis of the plants 106. Because the sensor group 224 is higher than the sensor group 222, this allows the one or more upper canopy climate sensors 230 and the upper canopy light sensor 232 to capture various measurements at a different height relative to the sensor group 222. If the platform 204 (and therefore the sensor group 224) is raised and lower via the lift 218, the one or more upper canopy climate sensors 230 and the upper canopy light sensor 232 can be used to capture various measurements at multiple different heights of the plants 106 relative to the sensor group 222. Note, however, that nothing prevents the sensor group 222 from being movable (right, left, up, down, forward, or backward).

The sensor groups 222 and 224 may include any suitable type(s) of sensors or other measurement devices. As particular examples, each sensor group 222 and 224 may include a temperature sensor, a humidity sensor, a carbon dioxide sensor, a PAR light sensor, a tilt sensor, and a red-green-blue (RGB) or other camera or other imaging sensor. Other or additional types of sensors that may be used in the sensor groups 222 and 224 may include spectrometers, multispectral cameras, hyperspectral cameras, infrared cameras, or thermal cameras. In general, any suitable physiological sensors, surface analysis sensors, chemical sensors, thermal sensors, microclimate sensors, image-based or video-based sensors, spectroscopy sensors, volatile organic compound sensors, canopy scanning sensors, or other sensors may be used in the sensor groups 222 and 224. Because the sensor groups 222 and 224 include at least one common type of sensor, the sensor groups 222 and 224 can be used to capture stereo-spatio-temporal data measurements associated with the plants 106.

The sensor groups 222 and 224 may also include sensors that are not common between the sensor groups 222 and 224. For example, the sensor group 222 may include a row detector sensor 234 and a row distance meter 236. The row detector sensor 234 can be used to sense when the mobile platform 114 turns onto or is traveling down a row of plants 106. This can be done in any suitable manner, such as by sensing a marking or other indicator on the ground of a greenhouse or other growing area 104a-104n, using an image processing or positioning technique, or using any other suitable technique. In some cases, the row detector sensor 234 can identify the specific row of plants 106 in which the mobile platform 114 is positioned. The row distance meter 236 measures how far along a row that the mobile platform 114 has traveled, such as by measuring the distance that the mobile platform 114 has traveled after turning onto a row. Collectively, the row detector sensor 234 and the row distance meter 236 can identify the position of the mobile platform 114 in a growing area 104a-104n, which may (among other things) allow the mobile platform 114 to associate data measurements with its location. Note, however, that any other suitable mechanism may be used here to identify a location of the mobile platform 114.

As another example, the sensor group 224 may include a camera 238, which can capture still, video, or thermal images of scenes in front of or around the mobile platform 114 (such as images of plants 106 being monitored). These images may be used for various purposes, such as to capture information about the plants 106, to capture information about where the mobile platform 114 is located, or to generate one or more graphical user interfaces. As a particular example, based on knowledge of the row location or other location of the mobile platform 114, the data processing platform 102 may generate a graphical user interface for the electronic device 210, where the graphical user interface includes an image captured by the camera 238 and markers or other indicators identifying plants 106 in the image to be inspected or operations to be performed on the plants 106 in the image. In some embodiments, the camera 238 may represent an immersive or other depth-based camera, such as a 360° immersive camera. The sensor group 224 may also include a plant health sensor 240, which may represent a sensor or collection of sensors that can gauge the overall health of the plants 106 being monitored.

In addition, the sensor group 224 may include a machine vision-based sensor 242, which can include or be associated with a dedicated graphics processing unit (GPU) 244. The machine vision-based sensor 242 and the GPU 244 can be used to capture and apply machine learning to images in order to identify one or more characteristics of the plants 106 being monitored. For example, one or more machine learning algorithms may be applied to captured images in order to identify or derive at least some of the plant production data, physical plant data, pest and disease data, crop work data, or crop treatment data. As a particular example, a neural network or other machine learning algorithm may be applied to still, video, or thermal images captured of various plants 106, where the neural network or other machine learning algorithm is trained to detect and count specific instances of fruits, vegetables, ornamental flowers, or other production items produced by the plants 106. The neural network or other machine learning algorithm may also be trained to identify, based on color or other factors, the ripeness or ready states of the fruits, vegetables, ornamental flowers, or other production items produced by the plants 106. This allows image processing to be used to automatically estimate production by the plants 106. As another particular example, a neural network or other machine learning algorithm may be applied to still, video, or thermal images captured of various plants 106, where the neural network or other machine learning algorithm is trained to count the number of plant stems in a given area (in order to identify the stem density in that area). Stem density is an indicator of the quality of the crop work being performed. Certain types of plants 106, such as cucumber and tomato plants, may be adjusted regularly in a process known as "lowering." Anomalies in crop density (such as packing plants 106 too densely) are known to impact plant production, and these conditions may be detected by or using the neural network or other machine learning algorithm. This allows image processing to be used to automatically identify characteristics related to crop work or other characteristics that might impact plant production.

Finally, the mobile platform 114 may include a height sensor 246, which can be used to measure the height of the movable portion of the mobile platform 114. This allows the mobile platform 114 or the data processing platform 102 to identify the actual Z-axis positions or other height-related positions of data measurements by the sensors mounted on the movable portion of the mobile platform 114. The height sensor 246 includes any suitable structure configured to measure height, such as a pressure sensor, accelerometer, or laser or ultrasound rangefinder pointed towards the ground. As a particular example, the height sensor 246 may include an accelerometer that measures a tilt of a portion of the scissor lift 218, where the tilt corresponds to a specific distance that the scissor lift 218 has raised the platform 204. Note that while shown as being positioned on the lift 218, the height sensor 246 may be placed in any other suitable location on the mobile platform 114, such as on the platform 204 or with the sensor group 224.

Note that while the sensor groups 222 and 224 here are shown as being positioned on the front of the mobile platform 114, the sensor groups 222 and 224 may be repositioned as needed or desired. For example, at least one of the sensor groups 222 and 224 may be repositioned toward the right or left side of the mobile platform 114 in order to facilitate measurements of plants 106. In other embodiments, the sensor groups 222 and 224 can be fixed and non-movable.

As shown in FIG. 3, various components of the mobile platform 114 are shown in block form. Here, the mobile platform 114 includes the sensor groups 222 and 224, the power supply 220, and the electronic device 210 (which in this example includes a display and supports a user interface). The mobile platform 114 also includes at least one processing device 302, which may form part of a computing or control system 303 for the mobile platform 114. The processing device 302 may execute instructions that can be loaded into a memory 304. The processing device 302 includes any suitable number(s) and type(s) of processors or other devices in any suitable arrangement. Example types of processing devices 302 include one or more microprocessors, microcontrollers, digital signal processors (DSPs), application specific integrated circuits (ASICs), field programmable gate arrays (FPGAs), or discrete circuitry. Example types of microprocessors may include at least one central processing unit (CPU), graphics processing unit (GPU), data processing unit (DPU), or Tensor processing unit (TPU). The memory 304 represents any suitable structure(s) configured to store and facilitate retrieval of information (such as data, program code, and/or other suitable information on a temporary or permanent basis). The memory 304 may represent a random access memory or any other suitable volatile or non-volatile storage device(s).

A data storage 306 may be used to store data used, generated, or collected by the processing device 302 or other components of the mobile platform 114. For example, the data storage 306 may be used to store data measurements collected using the sensors of the sensor groups 222 and 224. These data measurements may be stored and retrieved as needed, such as when the data measurements are stored during operation of the mobile platform 114 and then retrieved for transmission to the data processing platform 102. The data storage 306 represents any suitable structure(s) configured to store and facilitate retrieval of information, such as a random access memory, a read only memory, a hard drive, a solid-state drive, or a Flash memory.

A guidance/positioning system 308 can be configured to identify a location of the mobile platform 114 and to support navigation by the mobile platform 114. In some embodiments, the guidance/positioning system 308 produces location tags that can be associated with sensor data measurements, where the location tags identify X-Y or other positions (and possibly height measurements from the height sensor 246, if any) at which the data measurements are captured, and optionally transmitted along with the data measurements. The guidance/positioning system 308 includes any suitable structure configured to identify a location of the mobile platform 114, such as the row detector sensor 234 and the row distance meter 236. Other structures used in the guidance/positioning system 308 may include a GPS receiver or other satellite-based receiver, a UWB receiver, a visual odometer, an RFID device, or other device. Note that the guidance/positioning system 308 may operate by receiving incoming signals or other information to identify its location or by transmitting outgoing signals or other information that allow other components to identify its location.

A propulsion system 310 is configured to move the mobile platform 114, such as by causing the wheels 216 to rotate. The propulsion system 310 includes any suitable structure configured to propel or otherwise move the mobile platform 114, such as an electric motor. A communications unit 312 allows the mobile platform 114 to communicate information and data to one or more external systems or devices and/or to receive information or commands from one or more external systems or devices. In some embodiments, the communications unit 312 may include an external serial connection that is provided to allow a user to connect a personal computer (PC) or other device to the mobile platform 114, such as in order to modify the software or firmware on-board the mobile platform 114. Also, in some embodiments, the communications unit 312 may include at least one wireless radio or other wireless transmitter, receiver, or transceiver that allows wireless communications to and/or from the mobile platform 114. Also or alternatively, the mobile platform 114 may communicate via the mobile electronic device 210.

A treatment system 314 may be provided in the mobile platform 114 and can be configured to apply one or more treatment agents (such as at least one chemical pesticide and/or at least one biological control agent) to each of one or more plants 106 in one or more growing areas 104a-104n. The treatment system 314 includes any suitable structure configured to deliver one or more treatment agents to plants. Example embodiments of treatment systems are provided in U.S. patent application Ser. No. 16/990,212 (which was previously incorporated by reference). Note, however, that any other embodiments of the treatment system 314 may be used here.

Although FIGS. 2 and 3 illustrate one example of a mobile platform 114 supporting stereo-spatio-temporal crop condition measurements for plant growth and health optimization, various changes may be made to FIGS. 2 and 3. For example, the size, shape, and dimensions of the mobile platform 114 and its individual components may vary as needed or desired. Also, any number and type(s) of sensor(s) may be included in each sensor group 222 and 224, and the mobile platform 114 may include more than two sensor groups. Further, the use of a scissor lift 218 is one example mechanism for raising and lowering a portion of the mobile platform 114, and other mechanisms may be used to raise and lower or otherwise move at least the sensor group 224 (or the sensor group 224 may simply be fixed in a position offset from the sensor group 222 in at least one dimension). Moreover, stereo-spatio-temporal measurements may be captured using a similar arrangement of sensors but in different types of mobile platforms, including mobile platforms that are manually driven and robotic platforms that can move autonomously (such as by an on-board computing or control system 303 or a remote computing or control system). In addition, various components shown in FIGS. 2 and 3 may be combined, further subdivided, replicated, rearranged, or omitted and additional components may be added as needed or desired.

Figure 4:
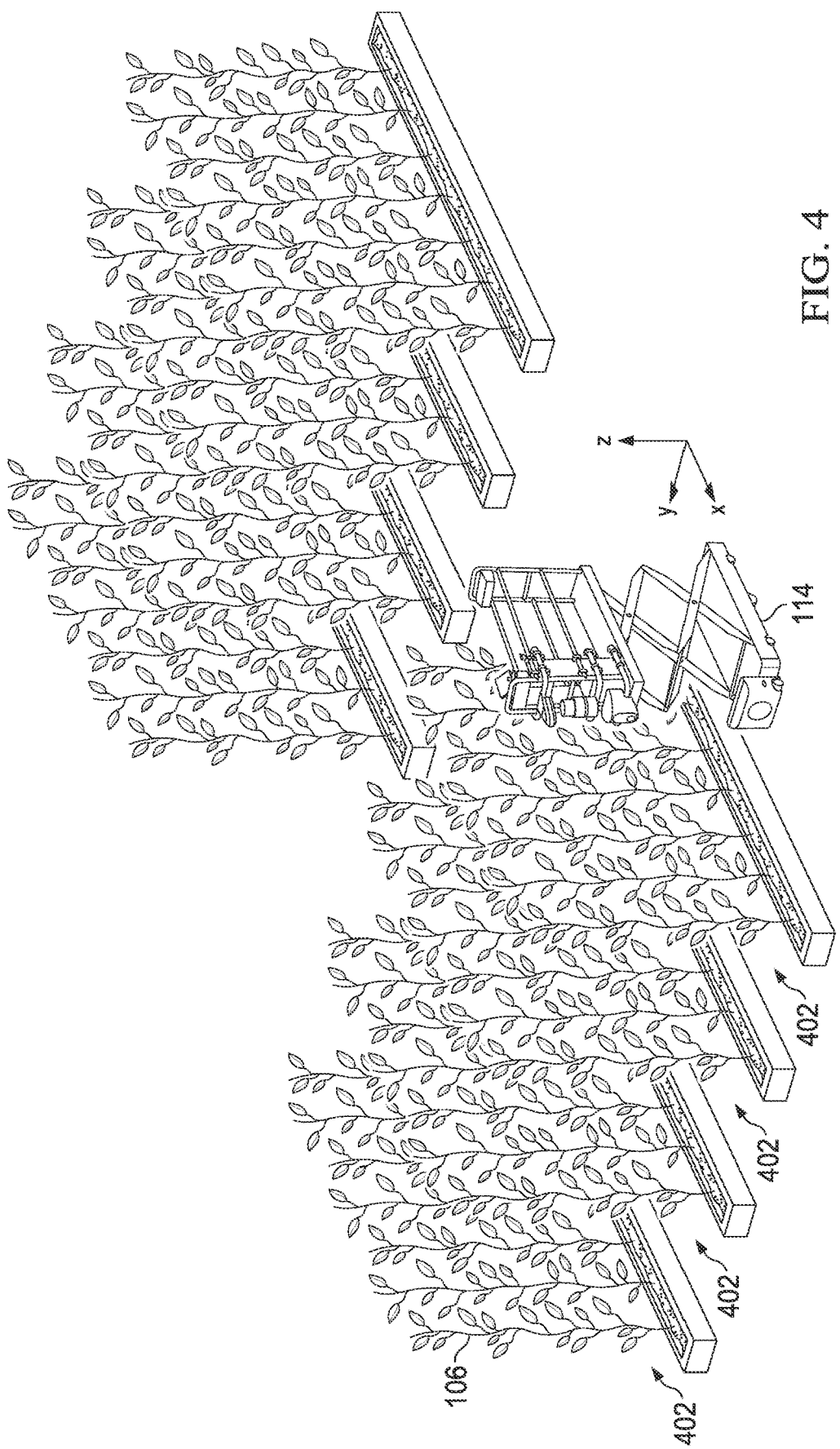
FIG. 4 illustrates an example use of a mobile platform supporting stereo-spatio-temporal crop condition measurements for plant growth and health optimization according to this disclosure.

FIG. 4 illustrates an example use of a mobile platform 114 supporting stereo-spatio-temporal crop condition measurements for plant growth and health optimization according to this disclosure. For ease of explanation, the use shown in FIG. 4 is described as involving the mobile platform 114 shown in FIGS. 2 and 3 in the system 100 shown in FIG. 1. However, the mobile platform 114 may be used in any suitable system(s) and with any suitable growing area(s).

As shown in FIG. 4, the mobile platform 114 is being used to monitor or inspect multiple plants 106 arranged in various rows 402 of plants. As can be seen here, the mobile platform 114 can move down each row 402 of plants in order to inspect the plants 106 in the rows 402. In this specific example, the rows 402 are said to extend lengthwise along an X-axis, and multiple rows 402 extend along a Y-axis. By moving the mobile platform 114, the sensors of the mobile platform 114 can capture spatio-temporal data measurements of the plants 106 in these two dimensions of the growing area 104a-104n.

In addition, as described above, the sensor groups 222 and 224 can be offset along a third axis called the Z-axis here. Also, in some cases, a portion of the mobile platform 114 can be raised and lowered, which allows one or more sensors of the sensor group 224 to be raised and lowered and to capture data measurements at multiple locations along the Z-axis. By using at least one common type of sensor in the sensor groups 222 and 224, this allows the mobile platform 114 to capture stereo-spatio-temporal data measurements of the plants 106. For instance, differences between sensor data measurements of the same type may be determined based on the sensor data measurements from the sensor groups 222 and 224, and these differences represent how at least one plant-related characteristic varies along at least part of the heights of the plants 106. Depending on the implementation, sensor data measurements may be identified at a fixed distance between the sensor groups 222 and 224, in discrete steps in height changes of the movable portion of the mobile platform 114, or continuously.

This allows data measurements to be obtained with much greater fidelity in the Z-axis, allowing larger portions of the plants 106 to be monitored. As described below, this also enables improved or new analyses that can be performed using the spatio-temporal data.

The ability to capture and process data measurements from sensor groups 222 and 224 that are offset along the Z-axis or other dimension(s) allows various useful measurements or other data to be obtained, such as the flux of change for one or more variables over at least part of the height of the plants 106, or to compare the differences in sensor data measurements over space and over time. Flux or differences can be calculated from a fixed point at the bottom of the plants 106 (as defined by the position(s) of the sensor(s) in the sensor group 222) to another or highest point (as defined by the fixed or highest position(s) of the sensor(s) in the sensor group 224). If desired, data measurements for positions in between sensor locations can be obtained via gap analysis fill, interpolation, or other techniques. Data, such as flux and difference data, may be useful or important since plants 106 can often have different microclimates at various parts of their canopies, and there are often boundary layers that define and influence the microclimates. The flux and differences between bottom and top portions or other portions of the plants 106 can provide an understanding of the climatic composition and exchanges between various layers of the plants 106.

Various advantages or benefits may be obtained using this type of approach. For example, this approach adds an additional measurement axis, such as by supporting sensor data measurements at different heights of the plants 106, which allows new or improved data analyses to be performed. For instance, sensor data measurements of the same data type at different heights allow various analyses, such as those based on eddy co-variants, to be considered in optimization calculations. Also, this approach can reduce the total cost of sensors and their associated installation costs in a growing area 104a-104n while keeping the same data fidelity, or this approach can improve the data fidelity for a significantly reduced cost (compared to traditional systems) by breaking the linear relationship between sensor cost and data fidelity. Very expensive sensors, which are not commercially viable today, can be made commercially viable for the same reason, again leading to new or further optimizations. Further, this approach allows sensors to be deployed in such a manner that they do not interfere with other operations in a growing area. In addition, improved data analysis techniques, such as artificial intelligence-based or other machine learning-based techniques, may be performed using the stereo-spatio-temporal data measurements.

Although FIG. 4 illustrates one example of a use of a mobile platform 114 supporting stereo-spatio-temporal crop condition measurements for plant growth and health optimization, various changes may be made to FIG. 4. For example, the mobile platform 114 may be used in any other suitable growing area 104a-104n in order to monitor plants 106 in any other suitable arrangement.

Figure 5A:
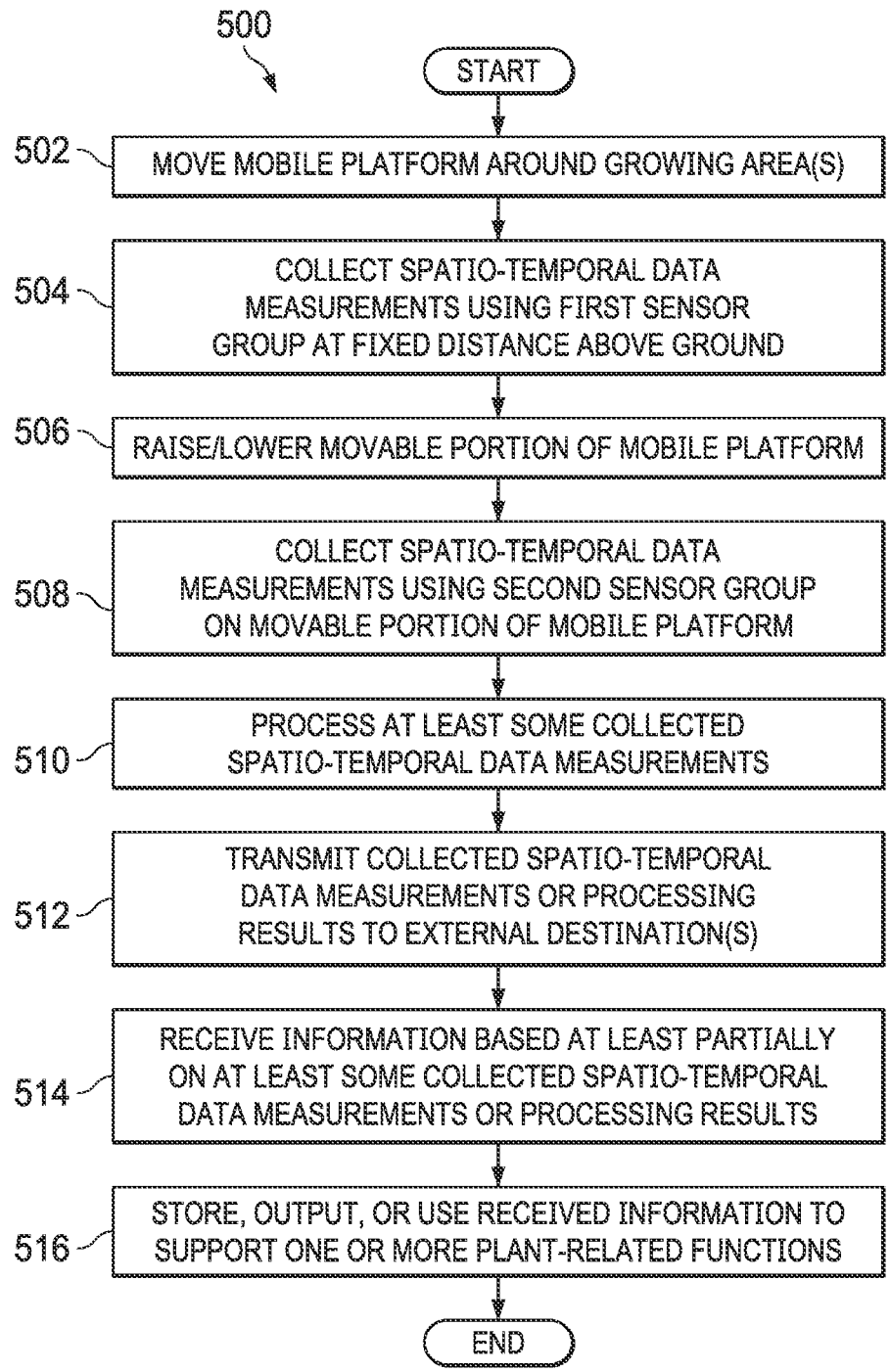
FIGS. 5A and 5B illustrate example methods for capturing stereo-spatio-temporal crop condition measurements to support plant growth and health optimization according to this disclosure.
Figure 5B:
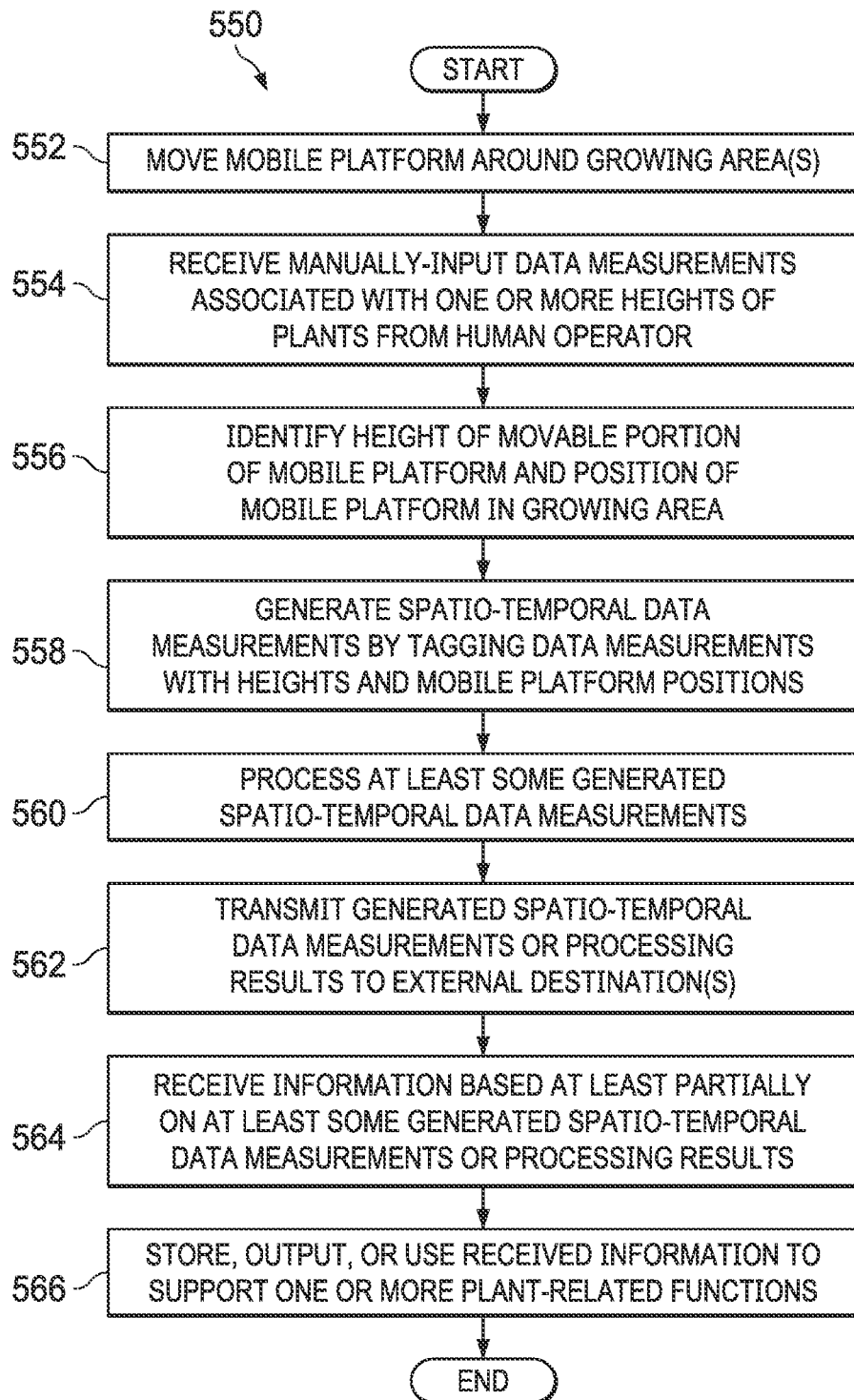

FIGS. 5A and 5B illustrate example methods 500 and 550 for capturing stereo-spatio-temporal crop condition measurements to support plant growth and health optimization according to this disclosure. For ease of explanation, the methods 500 and 550 shown in FIGS. 5A and 5B are described as involving the use of the mobile platform 114 shown in FIGS. 2 and 3 in the system 100 shown in FIG. 1. However, the methods 500 and 550 may involve the use of any suitable mobile platform(s) in any suitable system(s) and with any suitable growing area(s).

As shown in FIG. 5A, a mobile platform moves around at least one growing area at step 502. This may include, for example, a human operator (such as a human scout 110) driving the mobile platform 114 up and down rows 402 of plants 106 or otherwise around at least one growing area 104a-104n. This may alternatively include the data processing platform 102 or other component causing an automated mobile platform 114 to move up and down rows 402 of plants 106 or otherwise around at least one growing area 104a-104n.

Plant-related data measurements are collected using at least one sensor of a first sensor group at a fixed height above the ground at step 504. This may include, for example, one or more sensors of the sensor group 222 being used to capture plant production data, physical plant data, climate data, pest and disease data, crop work data, crop treatment data, or any other or additional plant-related data measurements. As a particular example, this may include sensors of the sensor group 222 capturing climatic- and lighting-related data measurements. The sensor group 222 can be mounted on a lower portion of the mobile platform 114 at a fixed distance from the ground, which allows these sensor data measurements to be captured at a known height of the plants 106 being inspected. These plant-related data measurements can be captured at different locations of the growing area(s) 104a-104n and at different times of day, season, or growing cycle. As a result, these plant-related data measurements represent multi-dimensional spatio-temporal data measurements.

A movable portion of the mobile platform can optionally be raised and lowered during operation of the mobile platform at step 506, and plant-related data measurements are collected using at least one sensor of a second sensor group at step 508. This may include, for example, one or more sensors of the sensor group 224 being used to capture plant production data, physical plant data, climate data, pest and disease data, crop work data, crop treatment data, or any other or additional plant-related data measurements. As a particular example, this may include sensors of the sensor group 224 capturing climatic- and lighting-related data measurements. This may further include the movable portion of the mobile platform 114 being raised and lowered using the lift 218. The sensor group 224 can be mounted at one or more known locations on the movable portion or other portion of the mobile platform 114, which allows these sensor data measurements to be captured at one or more known heights of the plants 106 being inspected (and the one or more known heights may be identified using the height sensor 246). Again, these plant-related data measurements can be captured at different locations of the growing area(s) 104*a*-104*n* and at different times of day, season, or growing cycle and, as a result, represent multi-dimensional spatio-temporal data measurements. However, these plant-related data measurements may represent measurements at one or more different heights relative to the data measurements captured by the sensor group 222.

Optionally, at least some of the collected plant-related data measurements may be processed by the mobile platform at step 510. This may include, for example, the processing device 302 or the GPU 244 of the mobile platform 114 processing collected data measurements in order to generate results based on the collected data measurements. At least some of the collected plant-related data measurements and/or at least some of the processing results can be transmitted to one or more external destinations at step 512. This may include, for example, the communications unit 312 of the mobile platform 114 transmitting at least some of the collected plant-related data measurements and/or at least some of the processing results to the data processing platform 102 or other destination(s).

The mobile platform or another device may receive information that is based at least partially on at least some of the collected plant-related data measurements and/or at least some of the processing results at step 514. This may include, for example, the communications unit 312 of the mobile platform 114 or the mobile electronic device 112, 210 receiving one or more graphical user interfaces or other information from the data processing platform 102. As particular examples, the information from the data processing platform 102 may identify one or more plants 106 that should be inspected for problems (such as one or more plants 106 to be inspected for at least one previously-detected, recently-detected, or projected pest or disease) or one or more actions to be performed by the human operator or by the mobile platform 114 (such as one or more treatments to be applied or crop work to be performed). The information can be stored, output, or used in any suitable manner at step 516. This may include, for example, the processing device 302 storing the information in the memory 304 or the data storage 306 of the mobile platform 114 or the mobile electronic device 112, 210 storing the information. This may also include the processing device 302 of the mobile platform 114 or a processor of the mobile electronic device 112, 210 presenting one or more graphical user interfaces to the human operator, such as a graphical user interface that includes an image of plants 106 and one or more indicators identifying one or more inspections or actions to occur for those plants 106. This may further include the processing device 302 of the mobile platform 114 causing the mobile platform 114 to perform one or more actions in an automated manner. Note that the received information may be used in any other or additional manner.

As shown in FIG. 5B, a mobile platform moves around at least one growing area at step 552. This may include, for example, a human operator (such as a human scout 110) driving the mobile platform 114 up and down rows 402 of plants 106 or otherwise around at least one growing area 104*a*-104*n*. Manually-input plant-related data measurements are received by the mobile platform from the human operator at step 554. This may include, for example, the processing device 302 of the mobile platform 114 receiving the manually-input data measurements from the human operator via the electronic device 210 during manual inspection of various plants 106. This may also include the human operator raising and lowering a movable portion of the mobile platform 114 as needed or desired to inspect the plants 106. The manually-input data measurements can be associated with any suitable plant-related characteristic(s), such as the presence and severity of any pests, diseases, or other problems. The manually-input data measurements can also be associated with one or more heights of the plants 106.

A height of the movable portion of the mobile platform and a position of the mobile platform in the growing area are identified at step 556. This may include, for example, the processing device 302 of the mobile platform 114 receiving a measured height from the height sensor 246 and a location of the mobile platform 114 from the guidance/positioning system 308 for each manually-input data measurement or each collection of manually-input data measurements. Spatio-temporal data measurements are generated by tagging each of the manually-input data measurements with its associated identified height and mobile platform position at step 558. This may include, for example, the processing device 302 of the mobile platform 114 storing each manually-input data measurement with its associated identified height and mobile platform position in the data storage 306.

Optionally, at least some of the generated spatio-temporal data measurements may be processed by the mobile platform at step 560. This may include, for example, the processing device 302 of the mobile platform 114 processing the generated spatio-temporal data measurements in order to generate results based on the data measurements. At least some of the generated spatio-temporal data measurements and/or at least some of the processing results can be transmitted to one or more external destinations at step 562. This may include, for example, the communications unit 312 of the mobile platform 114 transmitting at least some of the generated spatio-temporal data measurements and/or at least some of the processing results to the data processing platform 102 or other destination(s).

The mobile platform or another device may receive information that is based at least partially on at least some of the generated spatio-temporal data measurements and/or at least some of the processing results at step 564. This may include, for example, the communications unit 312 of the mobile platform 114 or the mobile electronic device 112, 210 receiving one or more graphical user interfaces or other information from the data processing platform 102. As particular examples, the information from the data processing platform 102 may identify one or more plants 106 that should be inspected for problems (such as one or more plants 106 to be inspected for at least one previously-detected, recently-detected, or projected pest or disease) or one or more actions to be performed by the human operator or by the mobile platform 114 (such as one or more treatments to be applied or crop work to be performed). The information can be stored, output, or used in any suitable manner at step 566. This may include, for example, the processing device 302 storing the information in the memory 304 or the data storage 306 of the mobile platform 114 or the mobile electronic device 112, 210 storing the information. This may also include the processing device 302 of the mobile platform 114 or a processor of the mobile electronic device 112, 210 presenting one or more graphical user interfaces to the human operator, such as a graphical user interface that includes an image of plants 106 and one or more indicators identifying one or more inspections or actions to occur for those plants 106. This may further include the processing device 302 of the mobile platform 114 causing the mobile platform 114 to perform one or more actions in an automated manner. Note that the received information may be used in any other or additional manner.

Although FIGS. 5A and 5B illustrate examples of methods 500 and 550 for capturing stereo-spatio-temporal crop condition measurements to support plant growth and health optimization, various changes may be made to FIGS. 5A and 5B. For example, while shown as a series of steps, various steps in each figure may overlap, occur in parallel, occur in a different order, occur any number of times, or be omitted, and additional steps may be added according to particular needs. As a particular example, data measurements by the second sensor group 224 may occur at a fixed height for the plants 106 without requirement raising or lowering of the movable portion of the mobile platform 114. Also, a combination of these approaches may be used, such as when both (i) data measurements from the sensor groups 222 and 224 and (ii) manually-input data measurements are received and used as shown here.

FIG. 6 illustrates an example device 600 supporting analyses of stereo-spatio-temporal crop condition measurements for plant growth and health optimization according to this disclosure. One or more instances of the device 200 may, for example, be used to at least partially implement the functionality of the data processing platform 102 of FIG. 1. However, the functionality of the data processing platform 102 may be implemented in any other suitable manner. Also, the same or similar arrangement of components as shown in FIG. 2 may be used to at least partially implement the functionality of one or more of the electronic devices 112, 122, 210 in FIGS. 1 and 2. However, the functionality of each electronic device 112, 122, 210 may be implemented in any other suitable manner.

As shown in FIG. 6, the device 600 denotes a computing device or system that includes at least one processing device 602, at least one storage device 604, at least one communications unit 606, and at least one input/output (I/O) unit 608. The processing device 602 may execute instructions that can be loaded into a memory 610. The processing device 602 includes any suitable number(s) and type(s) of processors or other devices in any suitable arrangement. Example types of processing devices 602 include one or more microprocessors, microcontrollers, DSPs, ASICs, FPGAs, or discrete circuitry. Example types of microprocessors may include at least one CPU, GPU, DPU, or TPU.

The memory 610 and a persistent storage 612 are examples of storage devices 604, which represent any structure(s) capable of storing and facilitating retrieval of information (such as data, program code, and/or other suitable information on a temporary or permanent basis). The memory 610 may represent a random access memory or any other suitable volatile or non-volatile storage device(s). The persistent storage 612 may contain one or more components or devices supporting longer-term storage of data, such as a read only memory, hard drive, Flash memory, or optical disc.

The communications unit 606 supports communications with other systems or devices. For example, the communications unit 606 can include a network interface card or a wireless transceiver facilitating communications over a wired or wireless network, such as a network 116. The communications unit 606 may support communications through any suitable physical or wireless communication link(s).

The I/O unit 608 allows for input and output of data. For example, the I/O unit 608 may provide a connection for user input through a keyboard, mouse, keypad, touchscreen, or other suitable input device. The I/O unit 608 may also send output to a display, printer, or other suitable output device. Note, however, that the I/O unit 608 may be omitted if the device 600 does not require local I/O, such as when the device 600 can be accessed remotely.

In some embodiments, the instructions executed by the processing device 602 can include instructions that implement the functionality of the data processing platform 102. For example, the instructions executed by the processing device 602 may cause the processing device 602 to obtain and store stereo-spatio-temporal data measurements (or processing results based on stereo-spatio-temporal data measurements) associated with plants 106 in one or more growing areas 104a-104n from one or more mobile platforms 114. The instructions executed by the processing device 602 may also cause the processing device 602 to perform one or more analyses of the stereo-spatio-temporal data measurements. Of course, the data processing platform 102 may receive additional stereo-spatio-temporal data measurements or other data (such as from the mobile electronic devices 112, 210 and/or the other data sources 118) and use the additional data in any suitable analyses as needed or desired. The instructions executed by the processing device 602 may further cause the processing device 602 to output results of the analyses or information based on the results of the analyses to the mobile platforms 114, the electronic devices 112, 122, 210, or other devices for use.

Although FIG. 6 illustrates one example of a device 600 supporting analyses of stereo-spatio-temporal crop condition measurements for plant growth and health optimization, various changes may be made to FIG. 6. For example, data processing platforms and mobile electronic devices can come in a wide variety of configurations, and FIG. 6 does not limit this disclosure to any particular data processing platform or mobile electronic device. Also, the data processing platform 102 may consider height-varying data measurements obtained from any other or additional sources (instead of or in addition to data measurements from one or more mobile platforms 114). This may or may not include human observations or other data measurements associated with different heights of the plants 106 being monitored.

There are a wide variety of analyses that may be performed by the data processing platform 102 based, at least in part, on stereo-spatio-temporal data measurements from one or more mobile platforms 114 or other data sources. The following discussion provide examples of the types of analyses that might be performed using stereo-spatio-temporal data measurements from one or more mobile platforms 114 or other data sources. However, other types of analyses may be performed as needed or desired. Also, in the discussion below, it may often be assumed that the stereo-spatio-temporal data measurements being processed are captured using one or more mobile platforms 114. However, stereo-spatio-temporal data measurements from any other or additional data sources (including human data sources) may be used here. In addition, note that the data processing platform 102 may be used to analyze stereo-spatio-temporal data measurements and make recommendations or trigger actions at individual times or in an intermittent or continuous manner as needed or desired.

As one example, the data processing platform 102 may be used to optimize the conditions for plant growth and health in one or more growing areas 104a-104n. For instance, the data processing platform 102 may detect increased humidity or decreased light penetration at the bottom of one or more plants 106, in which case the data processing platform 102 may recommend or trigger deleafing in order to avoid conditions that might facilitate disease growth. The data processing platform 102 may detect a gradient in light levels in order to better understand the need of the plants 106 for carbon dioxide (or vice versa), in which case the data processing platform 102 may recommend or trigger changes in light conditions or carbon dioxide levels. The data processing platform 102 may monitor the vertical temperature profiles of plants 106 (such as temperature profiles or differentials between flower heads and fruit or vegetables) in order to determine the pace of plant growth and the ripening of fruits or vegetables.

The data processing platform 102 may detect decreased light penetration at the mid-level of one or more plants 106 without excess humidity being present, in which case the data processing platform 102 may recommend or trigger changes to the operation or position of LED lights or other light sources in plant canopies to increase mid-canopy light penetration without de-leafing (to avoid affecting humidity). The data processing platform 102 may monitor the temperature gradients of the plants 106 and recommend or trigger changes to the operation of heat pipes underneath the plants 106 or at the heads of the plants 106 in order to achieve a desired temperature gradient, which can promote early vegetative growth (hotter at the bottom) or late season generative growth (hotter at the top).

The data processing platform 102 can compare plants 106 and groups of plants 106, such as by performing plant-to-plant comparisons and row-to-row comparisons, which generally increases the ability to optimize multiple metrics and may lead to more fidelity in actuator control or interventions. For instance, recommendations or triggered changes may be made to control or align individual fans, LEDs/other light sources, or sunshades on a per-plant or per-row basis more effectively. The data processing platform 102 can use humidity flux and evapotranspiration rates to recommend or trigger changes to irrigation. The data processing platform 102 can use canopy temperature flux and temperatures at the heads of the plants 106 to recommend or trigger changes to pollination or beehive density. The data processing platform 102 can use flux measurements to recommend or trigger other specific adjustments that were not possible previously due to a lack of information or data fidelity, such as confirming the bioavailability of nutritional materials provided through irrigation within the entire canopy of the plants 106.

As another example, the data processing platform 102 may be used to recognize and reduce non-uniformities introduced by greenhouse designs, control systems, or other characteristics of one or more growing areas 104a-104n. For example, humidity is typically higher by the walls and lower in the middle of a greenhouse. The data processing platform 102 may use humidity measurements to recommend or trigger different interventions in different portions of a growing area 104a-104n. As a particular example, the data processing platform 102 may use humidity measurements to recommend or trigger more deleafing of plants 106 around the edges of the growing area 104a-104n. Also, the orientation of the sun and a greenhouse or other growing area 104a-104n can create local hot spots or cold spots in different locations of the growing area 104a-104n at different times of day. Similarly, the presence of doors and windows can similarly create local hot spots or cold spots in different locations of the growing area 104a-104n at different times of day. The data processing platform 102 may use temperature measurements to recommend or trigger operations of individual fans, heaters, or sunshades to help combat the creation of local hot spots or cold spots in different locations of the growing area 104a-104n. In addition, plants 106 themselves can change local environments, such as by creating the most humid conditions at or near the bottom of the greenhouse or other growing area 104a-104n. The data processing platform 102 may use humidity measurements to recommend or trigger suitable intervention(s) in one or more portions of the growing area 104a-104n.

As yet another example, the data processing platform 102 may be used to recommend possible maintenance activities or to identify design changes to a greenhouse or other growing area (or to provide information to users for use in recommending or performing possible maintenance activities or identifying or making greenhouse or other growing area design changes). For instance, if humidity is higher at the bottom of one or more plants 106 than at the tops of the plants 106, this might indicate a leak in an irrigation system and the need for maintenance. Also, when deciding whether to install inner canopy lighting or heating technology, it might be useful to know the light levels at the tops and bottoms of plants 106 over the days of the year. Further, the data processing platform 102 can provide useful information to understand if new technology would be advantageous in a greenhouse or other growing area 104a-104n. As a particular example, vertical ventilation fans might offer an advantage in achieving a more uniform temperature gradient across a greenhouse or other growing area 104a-104n, and the use of height-based temperature measurements can identify what type of temperature gradients currently exist without that technology.

In addition, the data processing platform 102 may use machine learning, data mining, or other techniques to learn information and then put that information into use. Among other things, this may allow the data processing platform 102 to identify more favorable or more unfavorable conditions over time as more and more data is collected and processed. For instance, the data processing platform 102 may analyze climatic or lighting data to learn how flux or differences in data measurements across various variables may vary in cases where plants 106 are growing well and have good health and in cases where plants 106 are growing poorly and have poor health. This information can be used to establish correlations between flux balance and composition and the states of the plants 106, yields of the plants 106, etc. This information can also be used to understand the impacts of corrective actions (such as pesticide treatments, deleafing, or adjusting climatic conditions) on the flux or measurement differences and, by proxy, the states of the plants 106. These correlations can inform growers about the specific types of actions to take in order to maximize benefits and minimize costs and negative impacts.

As a specific example, it may be determined that the flux in relative humidity percentage has a direct correlation with powdery mildew and spider mite infestations and that proper deleafing has a direct impact on the relative humidity percentage. Based on this, relative humidity percentage may be used by the data processing platform 102 to make recommendations or trigger actions to control relative humidity percentage flux. In this example, understanding the infestation risk/severity and the correlation with relative humidity percentage flux can allow one of multiple corrective actions to be recommended or initiated, such as spraying the plants 106 with a pesticide or scheduling an early deleafing to reduce relative humidity percentage flux.

Each corrective action typically has a cost/benefit ratio associated with that corrective action. For example, spraying a pesticide may provide the benefits of rapid control and elimination of a problem, but the costs include material and labor to deploy the pesticide and stress on plants 106 due to pesticide application that lowers production. Early deleafing may provide the benefits of adjusting the relative humidity percentage flux and removing infected plant tissues, but the costs include the possibility of missing areas and leaving an infestation behind, labor, and requiring out-of-schedule work (which means other scheduled tasks may be put on hold). By giving growers greater flexibility in terms of what corrective actions are available, growers or the data processing platform 102 can make more informed decisions about which corrective action(s) should occur for each identified problem. For instance, the growers or the data processing platform 102 can take all of these matters into account (along with their costs, success rates, and potential improvements) in order to recommend or initiate the best course(s) of action.

The results of the analysis or analyses performed by the data processing platform 102 may be used in a wide variety of ways. For example, the data processing platform 102 may provide information to one or more electronic devices 112, 122, 210 for presentation to one or more users. The information may take the form of one or more graphical user interfaces, which may be used by the one or more users to interact with the data processing platform 102. Of course, any other suitable results produced by the data processing platform 102 may be used in any other suitable manner.

FIGS. 7A through 7D illustrate a first example type of graphical user interface generated based on an analysis of stereo-spatio-temporal crop condition measurements for plant growth and health optimization according to this disclosure. For ease of explanation, the graphical user interfaces shown in FIGS. 7A through 7D are described as being generated by the data processing platform 102 in the system 100 shown in FIG. 1. However, the graphical user interfaces may be generated by any suitable device in any suitable system(s) and with any suitable growing area(s).

Figure 7A:
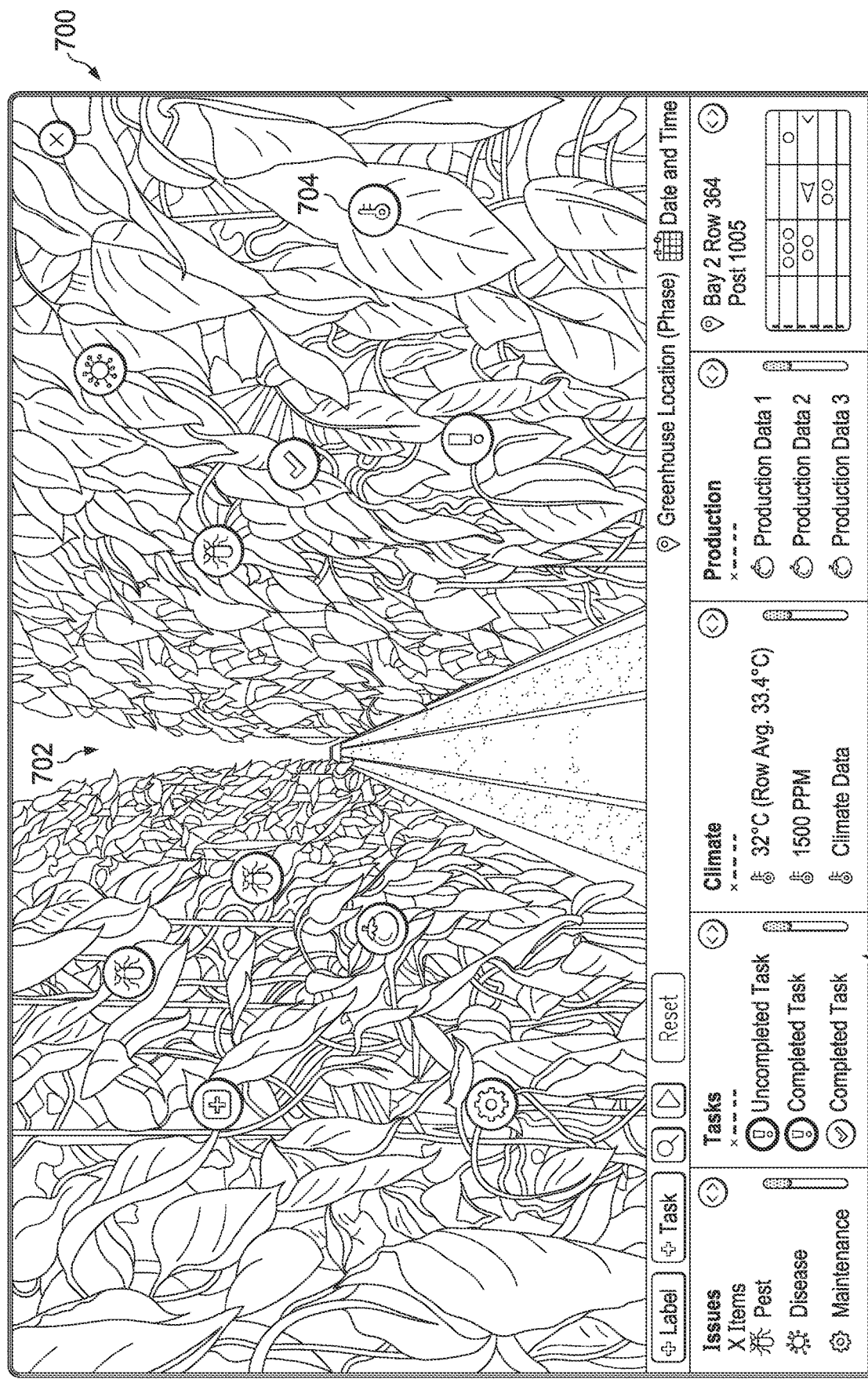
FIGS. 7A through 7D illustrate a first example type of graphical user interface generated based on an analysis of stereo-spatio-temporal crop condition measurements for plant growth and health optimization according to this disclosure.

As shown in FIG. 7A, a graphical user interface 700 can be used to present spatial information (based on an analysis of stereo-spatio-temporal crop condition measurements) that might be provided at one or more specific locations in a greenhouse or other growing area 104a-104n. Here, the graphical user interface 700 includes an image 702 of various plants arranged in rows in a greenhouse or other growing area 104a-104n. In some embodiments, the image 702 may be captured using the camera 238 of the mobile platform 114. The data processing platform 102 may receive the image 702 from the mobile platform 114 and use the location of the mobile platform 114 to identify which plants 106 are shown in the image 702 based on the location of the mobile platform 114. Any suitable image processing technique or other technique may be used by the data processing platform 102 to identify the specific plants 106 in the image 702.

The graphical user interface 700 also includes one or more indicators 704 presented over the image 702. Each indicator 704 can represent an issue associated with one or more plants 106 in the image 702. For example, at least one type of indicator 704 might identify at least one known pest, disease, or other problem associated with one or more plants 106 in the image 702. This type of indicator 704 or these types of indicators 704 might cause a human scout 110 to closely inspect each identified plant 106 or each identified area of a plant 106 to look for the pest(s), disease(s), or other problem(s). At least one other type of indicator 704 might identify at least one projected pest, disease, or other problem associated with one or more plants 106 in the image 702, meaning there might be at least one problem based on a projection calculated using prior data. Again, this type of indicator 704 or these types of indicators 704 might cause a human scout 110 to closely inspect each identified plant 106 or each identified area of a plant 106 to look for the pest(s), disease(s), or other problem(s). At least one other type of indicator 704 might indicate that crop work or some other specific action or actions are to occur for each identified plant 106 or each identified area of a plant 106. This type of indicator 704 or these types of indicators 704 might cause a human scout 110 to perform the specific action(s) for each identified plant 106 or each identified area of a plant 106.

A summary section 706 at the bottom of the graphical user interface 700 here may be used to present various information to the user. For example, the summary section 706 might identify one or more specific problems associated with the plants 106 identified in the image 702 and one or more actions to be performed on at least one of the plants 106 identified in the image 702. The summary section 706 might also identify climatic conditions and production counts associated with the plants 106 identified in the image 702. The summary section 706 might further identify a location of the mobile platform 114 or user in relation to plants 106 to be inspected or actions to be performed.

In some cases, the summary section 706 may be updated based on a selected one of the indicators 704, or a pop-up window may present additional information about a selected one of the indicators 704. In general, any desired information about the plants 106 or indicators 704 in the image 702 or other information may be presented in any suitable manner with the graphical user interface 700.

As can be seen in FIG. 7A, at least some of the indicators 704 appear at different heights of the plants 106 in the image 702. This is because the stereo-spatio-temporal data measurements permit analyses to be performed in the height axis of the plants 106 in addition to other axes (such as X and Y axes) of a growing area 104a-104n. One example result of this is that problems or corrective actions can be associated with specific portions of the plants 106 rather than with the entire plants 106 at given locations. This can greatly improve the monitoring of the plants and can help to improve or optimize the growth and health of the plants 106.

In some cases, this graphical user interface 700 might be shown on a display of one or more electronic devices 112, 210 to one or more workers as they are moving around a greenhouse or other growing area 104a-104n. The graphical user interface 700 (or the data processing platform 102) could also update the graphics in real-time to correspond to the workers' current location. In this way, additional insights about the plants 106 at the workers' current location could be shown.

Figure 7B:
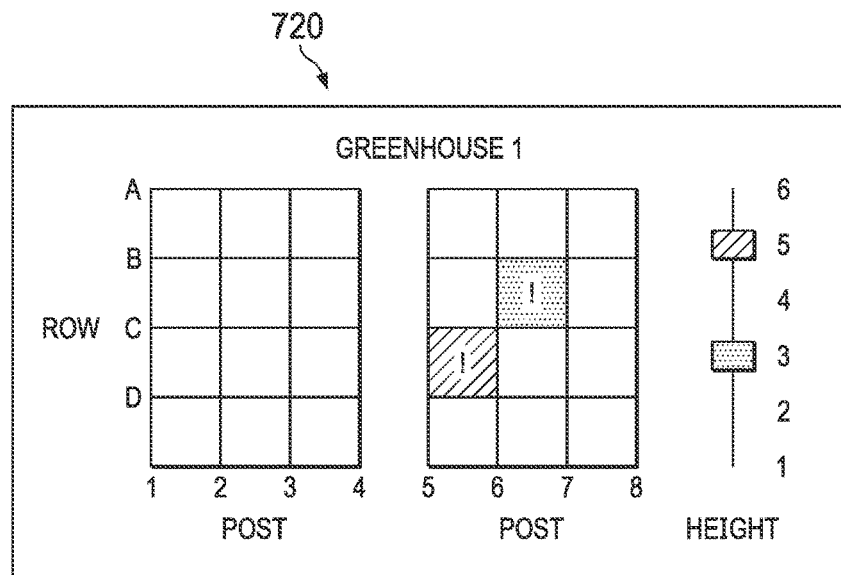
Figure 7C:
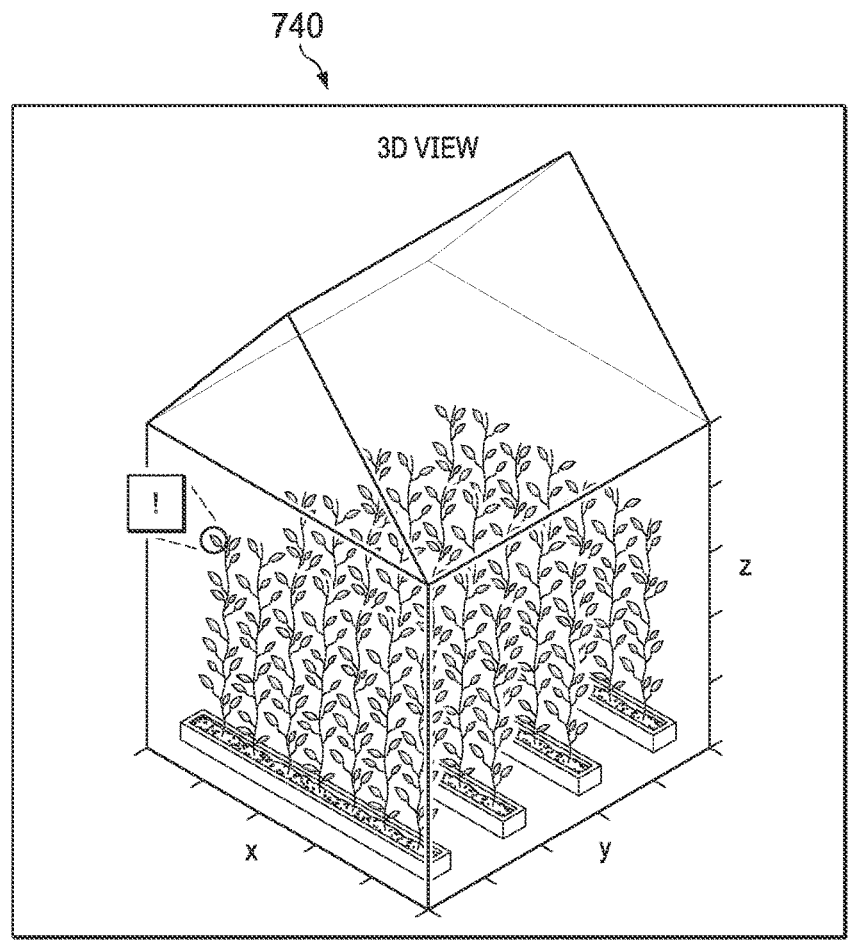
Figure 7D:
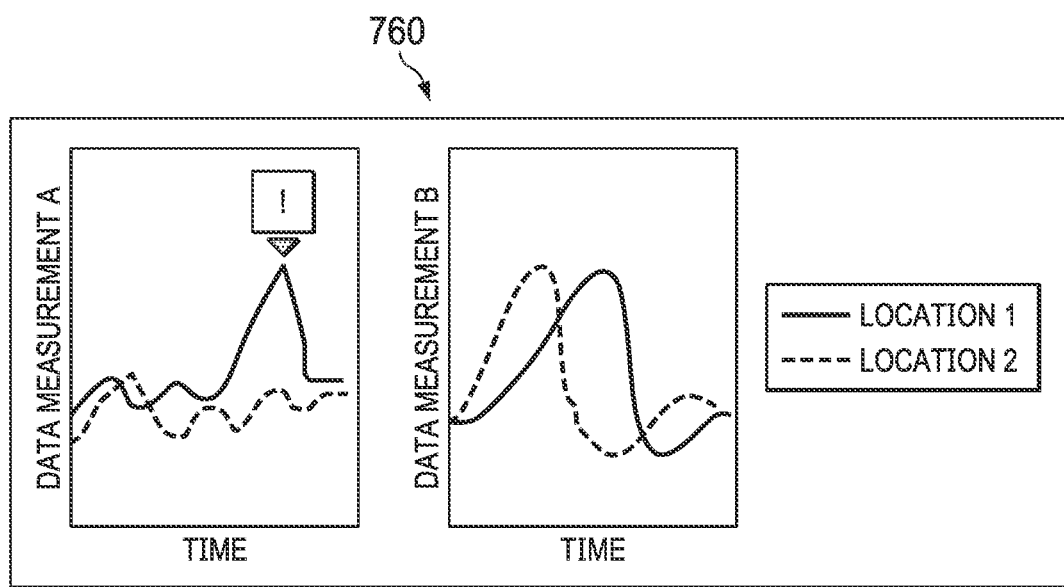

Note that the graphical user interface 700 shown in FIG. 7A has the form of a "virtual walk" in which the graphical user interface 700 is shown from the perspective of a person walking in the actual growing area. However, the same or similar contents of the graphical user interface 700 may be presented in any other suitable manner. For example, as shown in FIG. 7B, a graphical user interface 720 may present similar content in a two-dimensional format, where a slider or legend can identify how content varies by plant height (or other third dimension). As shown in FIG. 7C, a graphical user interface 740 may present similar content in a three-dimensional format. As shown in FIG. 7D, a graphical user interface 760 may present similar content in a time-series format for one or more specific locations. While graphs in FIG. 7D are shown as being separate, a single graph may also or alternatively be generated by overlaying the contents of the individual graphs. In each of these cases, one or more indicators (such as ones that are the same as or similar to the types of indicators 704 discussed above) may be presented in the graphical user interfaces 720, 740, 760.

Figure 8:
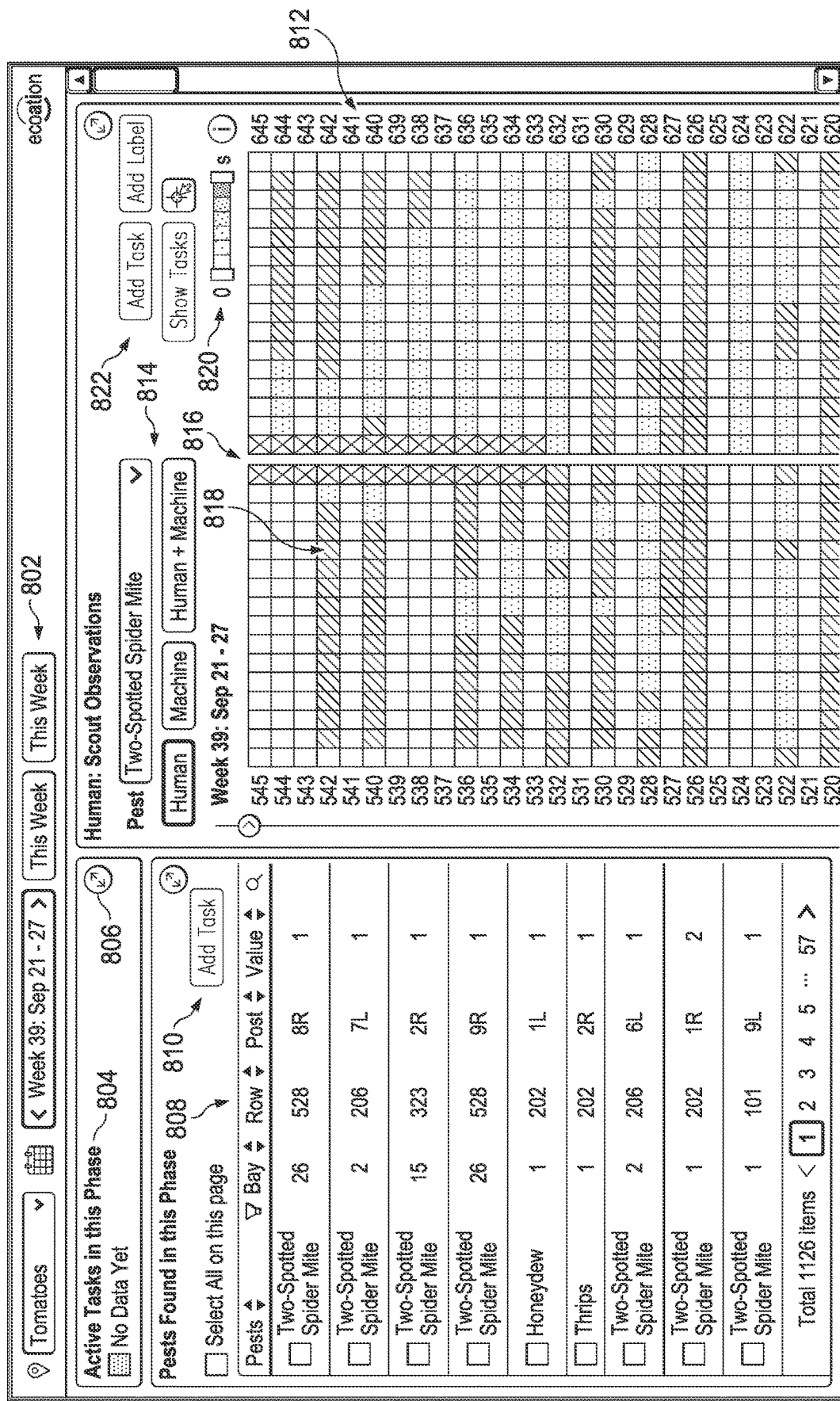
FIG. 8 illustrates a second example type of graphical user interface generated based on an analysis of stereo-spatio-temporal crop condition measurements for plant growth and health optimization according to this disclosure.

FIG. 8 illustrates a second example type of graphical user interface generated based on an analysis of stereo-spatio-temporal crop condition measurements for plant growth and health optimization according to this disclosure. For ease of explanation, the graphical user interface shown in FIG. 8 is described as being generated by the data processing platform 102 in the system 100 shown in FIG. 1. However, the graphical user interface may be generated by any suitable device in any suitable system(s) and with any suitable growing area(s).

As shown in FIG. 8, a graphical user interface 800 can be used to present information that is based on an analysis of stereo-spatio-temporal crop condition measurements. Here, the graphical user interface 800 includes a control section 802, which may be used to select data associated with at least one particular type of plant 106 (or for all plants 106 if desired) and a particular time period (which is referred to as a phase). For the selected plant type(s) and phase, the graphical user interface 800 can present a task section 804 that identifies active tasks for the selected type(s) of plant 106 and phase. The active tasks may, for instance, identify crop work or other operations to be performed for various plants 106 of the selected type(s). A control 806 may be used to expand and contract the size of the task section 804.

The graphical user interface 800 can also present a pest/disease section 808 that identifies any pests and diseases identified for the selected type(s) of plant 106 and phase. Each pest or disease can be identified by type, location, and severity. In this example, location is based on bay, row, and post numbers, and severity is expressed using numerical values from one to five (although location and severity can each be expressed in any other suitable manner). Controls 810 may be used to expand and contract the size of the pest/disease section 808 and to add entries to the pest/disease section 808.

An observation section 812 of the graphical user interface 800 presents results of one or more analyses of stereo-spatio-temporal data measurements associated with the selected type(s) of plant 106 and phase. In this example, the observation section 812 includes controls 814 that allow a user to (i) select a particular type of pest, disease, or other problem (or all problems if desired) and (ii) indicate whether only human-based observations, only machine-based observations, or both types of observations should be presented. Based on these selections, the observation section 812 can present a spatial overview 816 of all or a portion of a growing area 104a-104n, where the spatial overview 816 identifies where the selected type(s) of problem(s) actually exist or are predicted to exist in the growing area 104a-104n based on the selected type(s) of observations.

In this particular example, the spatial overview 816 includes various regions 818, where each region 818 is associated with a different plant 106 or collection of plants 106 in the growing area 104a-104n. In some cases, a region 818 may be empty if no human or machine inspections were performed for the associated plant(s) 106 during the selected phase, and a region 818 may have a specific color, shading, or other indicator if the associated plant(s) 106 did not suffer from the selected problem(s). If a region 818 is associated with one or more plants 106 that did suffer from the selected problem(s) during the selected phase, the region 818 can have a specific color, shading, or other indicator identifying the severity of the problem(s). A scale 820 can be displayed to inform the user how severity is presented in the spatial overview 816.

Controls 822 may be used to expand and contract the size of the observation section 812 and to add tasks and labels to one or more regions 818 selected by the user in the spatial overview 816. The controls 822 may also be used to show any tasks associated with one or more regions 818 in the spatial overview 816.

In some cases, this graphical user interface 800 might be shown on a terminal, such as an electronic device 122, to provide an overall spatial overview of an entire crop. Among other things, this might make it much easier to identify spatial issues, such as a broken greenhouse window or blind or the spread of a pest and disease through the greenhouse or other growing area 104a-104n.

Figure 9:
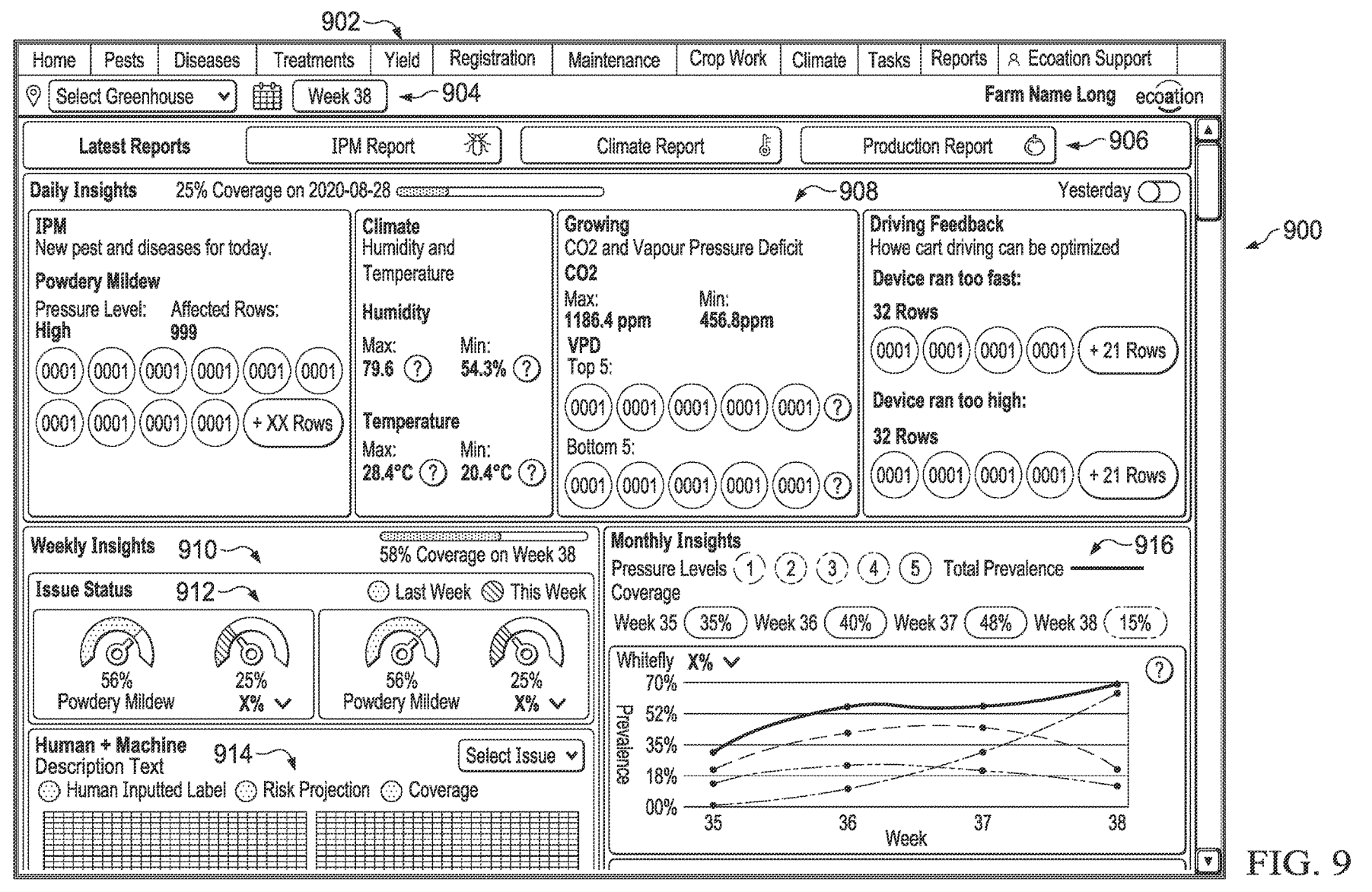

FIG. 9 illustrates a third example type of graphical user interface generated based on an analysis of stereo-spatio-temporal crop condition measurements for plant growth and health optimization according to this disclosure. For ease of explanation, the graphical user interface shown in FIG. 9 is described as being generated by the data processing platform 102 in the system 100 shown in FIG. 1. However, the graphical user interface may be generated by any suitable device in any suitable system(s) and with any suitable growing area(s).

As shown in FIG. 9, a graphical user interface 900 can again be used to present information that is based on an analysis of stereo-spatio-temporal crop condition measurements. Here, the graphical user interface 900 includes various tabs 902, which allow a user to select and view information about various features or aspects of one or more growing areas 104a-104n. A control section 904 may be used to select data associated with at least one particular growing area 104a-104n and a time period/phase. For the selected growing area(s) and phase, the graphical user interface 900 can present controls 906 that identify different reports available for viewing, such as an integrated pest management (IPM) report, climate report, or production report.

A daily insights section 908 can present information and recommendations to one or more users. In this example, the daily insights section 908 can include information identifying new pests, diseases, or other problems identified for the selected growing area(s) 104a-104n. The daily insights section 908 can also include information identifying overall climatic conditions and other growing conditions for the selected growing area(s) 104a-104n. The daily insights section 908 can further include information identifying feedback or recommendations, such as indications that certain measurements were obtained using a mobile platform 114, cart, or other device that moved too fast or was too high/low. The information in the daily insights section 908 may be related to data collected daily or most frequently in the selected growing area(s) 104a-104n.

A weekly insights section 910 can present information collected over a longer period of time (weekly in this case). In this example, the weekly insights section 910 includes various dashboards 912 that identify how conditions (such as one or more specific pests, diseases, or other problems) have changed for the given week compared to the prior week. The weekly insights section 910 also includes a spatial overview 914, which can be the same as or similar to the spatial overview 816 described above.

A monthly insights section 916 can present information collected over an even longer period of time (monthly in this case). In this example, the monthly insights section 916 includes various charts showing how one or more specific pests, diseases, or other problems have varied over time for the selected growing area(s) 104a-104n.

In some cases, this graphical user interface 900 might be shown on a terminal, such as an electronic device 122, to provide an overall time-series overview of selected data. Among other things, this might make it much easier to identify certain issues, such as those tied to time-of-day or seasonal cycles (like broken heating or lights). Note that the graphical user interface 900 in FIG. 9 is relatively wide, which may be the format used with devices like tablet, laptop, or desktop computers. For mobile smartphones or other devices with smaller screens, the contents of the graphical user interface 900 might be rearranged, such as by using a more vertical arrangement of content.

Although FIGS. 7A through 7D, 8, and 9 illustrate example types of graphical user interfaces generated based on an analysis of stereo-spatio-temporal crop condition measurements for plant growth and health optimization, various changes may be made to these figures. For example, the content and the arrangement of that content in each graphical user interface can vary as needed or desired. Also, any other suitable graphical user interface or other outputs may be produced by the data processing platform 102 for use by one or more users.

Figure 10:
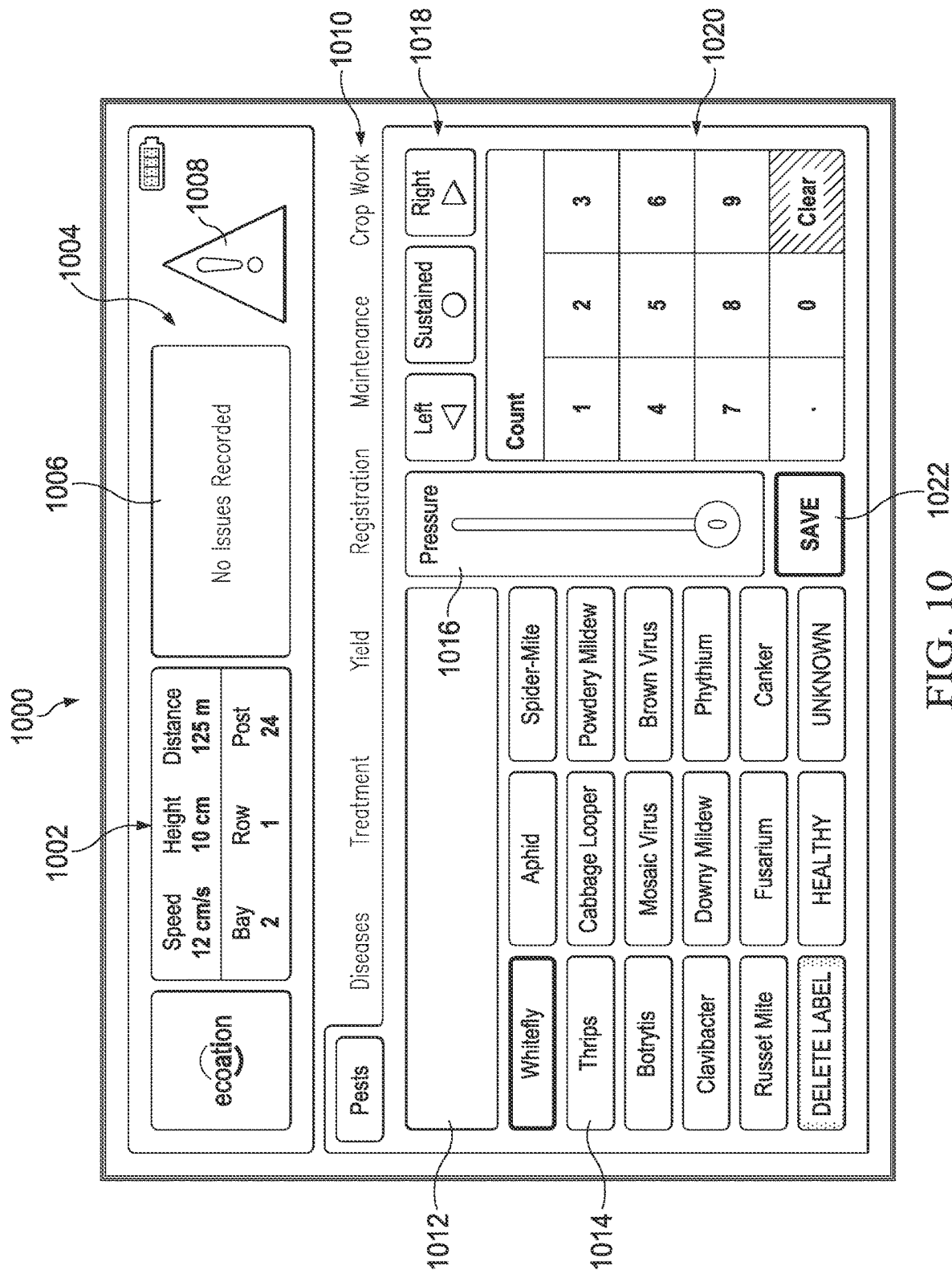
FIG. 10 illustrates an example graphical user interface for receiving human observation data measurements to support analysis of stereo-spatio-temporal crop condition measurements for plant growth and health optimization according to this disclosure.

FIG. 10 illustrates an example graphical user interface 1000 for receiving human observation data measurements to support analysis of stereo-spatio-temporal crop condition measurements for plant growth and health optimization according to this disclosure. The graphical user interface 1000 may, for example, be presented on an electronic device 112, 210 for use by a human operator of a mobile platform 114 or other personnel. For ease of explanation, the graphical user interface shown in FIG. 10 is described as being generated by the data processing platform 102 in the system 100 shown in FIG. 1. However, the graphical user interface may be generated by any suitable device in any suitable system(s) and with any suitable growing area(s).

As shown in FIG. 10, the graphical user interface 1000 includes a mobile platform section 1002, which identifies various information about the mobile platform 114. In this example, the mobile platform section 1002 identifies the speed of the mobile platform 114, the current height of the movable portion of the mobile platform 114, the distance traveled by the mobile platform 114 down a row, and a location of the mobile platform 114. Also, in this example, the location of the mobile platform 114 is expressed using bay, row, and post numbers. Note, however, that any other or additional information related to the mobile platform 114 may be presented here.

An issues section 1004 identifies any known plant-related issues associated with one or more plants 106 that are in the vicinity of the location of the mobile platform 114. For example, a box 1006 in the issues section 1004 may present a text-based description of any known issues associated with one or more plants 106 in the vicinity of the location of the mobile platform 114 (or an indication that no issues are currently active). An icon 1008 in the issues section 1004 can change colors, flash, or otherwise provide an indication when at least one problem is identified in the box 1006, such as when a user has driven the mobile platform 114 into part of a growing area 104a-104n in which one or more plants 106 have at least one active issue (such as at least one pest, disease, treatment, crop work, or other action to be performed by the user).

A menu 1010 allows the user to identify a specific type of data to be manually provided by the user. In this example, it is assumed that the user is entering information about a pest, although the same, similar, or different I/O mechanisms might be used to receive data from the user related to other entries in the menu. For the "pests" option in the menu 1010, the graphical user interface 1000 includes a text box 1012 in which the user may enter any desired text-based information (such as a manual observation of a pest or other plant-related information). Buttons 1014 allow the user to select a particular pre-defined label for a human observation. Since the "pests" option is selected in the menu 1010, the buttons 1014 can identify specific types of pests that might be selected by the user, although other types of buttons may be provided for other types of human observations. This allows the user to quickly and easily provide a human observation data measurement related to a specific type of pest or other measurement. Additional buttons 1014 can be used by the user to identify the overall status of plants 106 and to delete a label (one of the buttons 1014).

For a selected pest, the graphical user interface 1000 provides a slider 1016 that can be used by the user to identify the overall pressure of the selected pest in the current location. In this case, the slider 1016 can be moved up and down to define a specific pest pressure, although other mechanisms (such as a text box) might be used. Location controls 1018 may be used by the user to define where the specific pest is located, which in this example includes a left side, a right side, or both sides (sustained). Note, however, that any other or additional location controls may be provided here to identify any other or additional locations. A soft numeric keypad 1020 allows the user to enter a numerical value defining a count or number of pests identified by the user (assuming instances of the selected pest can be separately counted). If the selected pest cannot be separately counted (such as in the case of mildew), a different mechanism may be used to identify the extent or severity of the pest.

A save button 1022 allows the user to save the information in the graphical user interface 1000. As described in this document, saving a human observation may allow one or more spatio-temporal data measurements (and possibly one or more stereo-spatio-temporal data measurements) to be obtained by the data processing platform 102. The actual generation of the spatio-temporal data measurements may occur in the mobile platform 114, in the electronic device 112, 210, in the data processing platform 102, or in any other suitable location.

Although FIG. 10 illustrates one example of a graphical user interface 1000 for receiving human observation data measurements to support analysis of stereo-spatio-temporal crop condition measurements for plant growth and health optimization, various changes may be made to FIG. 10. For example, the content and the arrangement of that content in the graphical user interface 1000 can vary as needed or desired. Also, any other suitable graphical user interface or other mechanisms may be used to obtain human observations. In addition, the specific I/O mechanisms shown here (such as text boxes, buttons, sliders, and soft keypads) can easily vary in other implementations.

Figure 11:
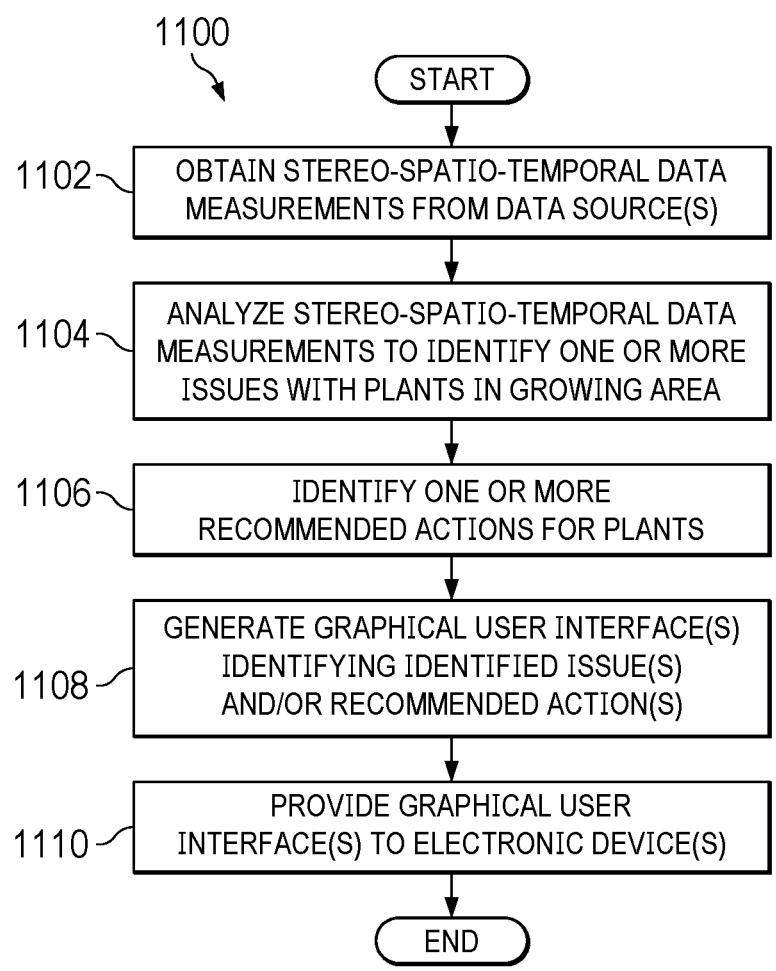
FIG. 11 illustrates an example method for analyzing stereo-spatio-temporal crop condition measurements to support plant growth and health optimization according to this disclosure.

FIG. 11 illustrates an example method 1100 for analyzing stereo-spatio-temporal crop condition measurements to support plant growth optimization according to this disclosure. For ease of explanation, the method 1100 shown in FIG. 11 is described as involving the use of the data processing platform 102 shown in FIG. 6 in the system 100 shown in FIG. 1. However, the method 1100 may involve the use of any data processing platform(s) in any suitable system(s) and with any suitable growing area(s).

As shown in FIG. 11, stereo-spatio-temporal data measurements for plants in at least one growing area are obtained from one or more data sources at step 1102. This may include, for example, the communications unit 606 of the data processing platform 102 receiving the stereo-spatio-temporal data measurements from one or more mobile platforms 114, electronic devices 112, 210, or other suitable data source(s). Note that the data processing platform 102 may receive any additional plant-related information in addition to the stereo-spatio-temporal data measurements. This may also include the processing device 602 of the data processing platform 102 storing the obtained data, such as in the memory 610 or persistent storage 612.

The stereo-spatio-temporal data measurements are analyzed to identify one or more issues with one or more of the plants in the at least one growing area at step 1104, and one or more recommended actions are identified (and optionally triggered automatically) at step 1106. This may include, for example, the processing device 602 of the data processing platform 102 analyzing the stereo-spatio-temporal data measurements (and possibly other data) to identify one or more problems associated with one or more of the plants 106 or to identify one or more corrective actions to occur involving one or more of the plants 106. As described above, the analysis of stereo-spatio-temporal data measurements can take various forms, and at least some of the analyses may be based on the flux or differences between measurements of a common data type at different heights of the plants 106. Also, an identification of the recommended action(s) may involve analyzing multiple types of corrective actions, such as based on their cost/benefit ratios, in order to select which action(s) to recommend.

The identified issue(s) and recommended action(s) may be used in any suitable manner. For example, in FIG. 11, at least one graphical user interface is generated at step 1108 and provided to at least one electronic device for presentation at step 1110. The graphical user interface may include information identifying the identified issue(s) and recommended action(s), request approval for performing the recommended action(s), or contain any other suitable contents in any suitable arrangement.

Although FIG. 11 illustrates one example of a method 1100 for analyzing stereo-spatio-temporal crop condition measurements to support plant growth and health optimization, various changes may be made to FIG. 11. For example, while shown as a series of steps, various steps in FIG. 11 may overlap, occur in parallel, occur in a different order, occur any number of times, or be omitted, and additional steps may be added according to particular needs. As a particular example, the data processing platform 102 may perform various actions without interacting with one or more users via one or more graphical user interfaces.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive (HDD), a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable storage device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
at least one processor configured to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;

analyze the stereo-spatio-temporal data measurements to identify one or more actual or potential pests or diseases associated with one or more of the plants; and generate a graphical user interface identifying at least one of the one or more actual or potential pests or diseases with the one or more plants;

wherein the first and second spatio-temporal data measurements of each stereo-spatio- temporal data measurement are associated with at least one common plant characteristic and different three-dimensional positions within the growing area taken at one or more known times;

wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and wherein the graphical user interface comprises:
the image;
at least one indicator identifying the at least one of the one or more actual or potential pests or diseases, each indicator placed in the image in association with the associated plant that has or may have the associated actual or potential pest or disease; and
a summary section displayed adjacent to the image and providing details related to the at least one indicator identifying the at least one of the one or more actual or potential pests or diseases.

2. The apparatus of claim 1, wherein the graphical user interface comprises at least some of the stereo-spatio-temporal data measurements in a spatial overview of the growing area and additional information related to the growing area.

3. The apparatus of claim 1, wherein the at least one processor is further configured to identify one or more corrective actions that at least partially resolve the one or more actual or potential pests or diseases associated with the one or more plants.

4. The apparatus of claim 1, wherein the at least one processor is further configured to identify, for each of the one or more actual or potential pests or diseases, a portion of the associated plant that is or may be suffering from the associated actual or potential pest or disease.

5. The apparatus of claim 1, wherein at least some of the first and second spatio-temporal data measurements comprise human observation data measurements.

6. An apparatus comprising:
at least one processor configured to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;
analyze the stereo-spatio-temporal data measurements to identify one or more actual or potential pests or diseases associated with one or more of the plants; and generate a graphical user interface identifying at least one of the one or more actual or potential pests or diseases with the one or more plants;

wherein the first and second spatio-temporal data measurements of each stereo-spatio- temporal data measurement are associated with at least one common plant characteristic and different three-dimensional positions within the growing area taken at one or more known times;

wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and wherein the graphical user interface comprises:
the image;
at least one first indicator identifying the at least one of the one or more actual or potential pests or diseases, each first indicator placed in the image in association with the associated plant that has or may have the associated actual or potential pest or disease;
a two-dimensional or three-dimensional representation of at least part of the growing area; and
at least one second indicator identifying the at least one of the one or more actual or potential pests or diseases, each second indicator placed in the representation in association with a location of the associated plant that has or may have the associated actual or potential pest or disease.

7. An apparatus comprising:
at least one processor configured to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;
analyze the stereo-spatio-temporal data measurements to identify one or more actual or potential pests or diseases associated with one or more of the plants; and
generate a graphical user interface identifying at least one of the one or more actual or potential pests or diseases with the one or more plants;

wherein the first and second spatio-temporal data measurements of each stereo-spatio- temporal data measurement are associated with at least one common plant characteristic and different three-dimensional positions within the growing area taken at one or more known times;

wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and wherein the graphical user interface comprises:
the image;
at least one first indicator identifying the at least one of the one or more actual or potential pests or diseases, each first indicator placed in the image in association with the associated plant that has or may have the associated actual or potential pest or disease;
one or more graphs containing at least some of the stereo-spatio-temporal data measurements over time; and
at least one second indicator identifying the at least one of the one or more actual or potential pests or diseases, each second indicator placed in an associated graph in association with a data measurement of the associated plant that has or may have the associated actual or potential pest or disease.

8. An apparatus comprising:
at least one processor configured to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;
analyze the stereo-spatio-temporal data measurements to identify one or more actual or potential pests or diseases associated with one or more of the plants
identify one or more corrective actions that at least partially resolve the one or more actual or potential pests or diseases associated with the one or more plants; and
generate a graphical user interface identifying at least one of the one or more actual or potential pests or diseases with the one or more plants;
wherein the first and second spatio-temporal data measurements of each stereo-spatio- temporal data measurement are associated with at least one common plant characteristic and different three-dimensional positions within the growing area taken at one or more known times;
wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and
wherein the graphical user interface comprises:
the image;
at least one first indicator identifying the at least one of the one or more actual or potential pests or diseases, each first indicator placed in the image in association with the associated plant that has or may have the associated actual or potential pest or disease; and
at least one second indicator identifying at least one of the one or more corrective actions, each second indicator placed in the graphical user interface in association with the associated plant to which the associated corrective action is to be applied.

9. An apparatus comprising:
at least one processor is configured to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;
analyze the stereo-spatio-temporal data measurements to identify one or more actual or potential pests or diseases associated with one or more of the plants;
identify at least one of the one or more actual or potential pests or diseases based on a flux or a difference in a specified plant-related characteristic along at a plurality of heights of one or more of the plants; and
generate a graphical user interface identifying at least one of the one or more actual or potential pests or diseases with the one or more plants;
wherein the first and second spatio-temporal data measurements of each stereo-spatio- temporal data measurement are associated with at least one common plant characteristic and different three-dimensional positions within the growing area taken at one or more known times;
wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and
wherein the graphical user interface comprises:
the image; and
at least one indicator identifying the at least one of the one or more actual or potential pests or diseases, each indicator placed in the image in association with the associated plant that has or may have the associated actual or potential pest or disease.

10. An apparatus comprising:
at least one processor configured to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;
analyze the stereo-spatio-temporal data measurements to identify one or more actual or potential pests or diseases associated with one or more of the plants;
identify, for each of the one or more actual or potential pests or diseases, a portion of the associated plant that is or may be suffering from the associated actual or potential pest or disease;
for each actual or potential pest or disease, identify a corrective action to be applied to the portion of the plant that is or may be suffering from the associated actual or potential pest or disease; and
generate a graphical user interface identifying at least one of the one or more actual or potential pests or diseases with the one or more plants;
wherein the first and second spatio-temporal data measurements of each stereo-spatio-temporal data measurement are associated with at least one common plant characteristic and different three-dimensional positions within the growing area taken at one or more known times;

wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and wherein the graphical user interface comprises:
the image; and
at least one indicator identifying the at least one of the one or more actual or potential pests or diseases, each indicator placed in the image in association with the associated plant that has or may have the associated actual or potential pest or disease.

11. A method comprising:

obtaining an image capturing at least part of a growing area;

obtaining stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;

analyzing the stereo-spatio-temporal data measurements to identify one or more actual or potential pests or diseases associated with one or more of the plants; and generating a graphical user interface identifying at least one of the one or more actual or potential pests or diseases with the one or more plants;

wherein the first and second spatio-temporal data measurements of each stereo-spatio-temporal data measurement are associated with at least one common plant characteristic and different three-dimensional positions within the growing area taken at one or more known times;

wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and wherein the graphical user interface comprises:
the image;
at least one first indicator identifying the at least one of the one or more actual or potential pests or diseases, each first indicator placed in the image in association with the associated plant that has or may have the associated actual or potential pest or disease; and
a summary section displayed adjacent to the image and providing details related to the at least one first indicator identifying the at least one of the one or more actual or potential pests or diseases.

12. The method of claim 11, wherein the graphical user interface comprises:
a two-dimensional or three-dimensional representation of at least part of the growing area; and
at least one second indicator identifying the at least one of the one or more actual or potential pests or diseases, each second indicator placed in the representation in association with a location of the associated plant that has or may have the associated actual or potential pest or disease.

13. The method of claim 11, wherein the graphical user interface comprises:
one or more graphs containing at least some of the stereo-spatio-temporal data measurements over time; and
at least one second indicator identifying the at least one of the one or more actual or potential pests or diseases, each second indicator placed in an associated graph in association with a data measurement of the associated plant that has or may have the associated actual or potential pest or disease.

14. The method of claim 11, wherein the graphical user interface comprises at least some of the stereo-spatio-temporal data measurements in a spatial overview of the growing area and additional information related to the growing area.

15. The method of claim 11, further comprising:
identifying one or more corrective actions that at least partially resolve the one or more actual or potential pests or diseases associated with the one or more plants.

16. The method of claim 15, wherein the graphical user interface comprises at least one second indicator identifying at least one of the one or more corrective actions, each second indicator placed in the graphical user interface in association with the associated plant to which the associated corrective action is to be applied.

17. The method of claim 11, wherein at least one of the one or more actual or potential pests or diseases is identified based on a flux or a difference in a specified plant-related characteristic along at a plurality of heights of one or more of the plants.

18. The method of claim 11, further comprising:
identifying, for each of the one or more actual or potential pests or diseases, a portion of the associated plant that is or may be suffering from the associated actual or potential pest or disease.

19. The method of claim 18, wherein, for each actual or potential pest or disease, a corrective action to be applied to the portion of the plant that is or may be suffering from the associated actual or potential pest or disease is identified.

20. The method of claim 11, wherein at least some of the first and second spatio-temporal data measurements comprise human observation data measurements.

21. A non-transitory computer readable medium containing instructions that when executed cause at least one processor to:
obtain an image capturing at least part of a growing area;
obtain stereo-spatio-temporal data measurements of plants in the growing area, the stereo-spatio-temporal data measurements comprising (i) first spatio-temporal data measurements of the plants in the growing area and (ii) second spatio-temporal data measurements of the plants in the growing area;
analyze the stereo-spatio-temporal data measurements to identify one or more actual or potential pests or diseases associated with one or more of the plants; and
generate a graphical user interface identifying at least one of the one or more actual or potential pests or diseases with the one or more plants;
wherein the first and second spatio-temporal data measurements of each stereo-spatio-temporal data measurement are associated with at least one common plant characteristic and different three-dimensional positions within the growing area taken at one or more known times;

wherein at least some of the first and second spatio-temporal data measurements comprise data measurements simultaneously captured at different heights by (i) at least one first sensor fixedly mounted on a base of a mobile platform and (ii) at least one second sensor mounted on a platform of the mobile platform that is movable relative to the base and used to identify the one or more actual or potential pests or diseases associated with one or more of the plants; and wherein the graphical user interface comprises:
the image;
at least one first indicator identifying the at least one of the one or more actual or potential pests or diseases, each first indicator placed in the image in association with the associated plant that has or may have the associated actual or potential pest or disease;
one or more graphs containing at least some of the stereo-spatio-temporal data measurements over time; and
at least one second indicator identifying the at least one of the one or more actual or potential pests or diseases, each second indicator placed in an associated graph in association with a data measurement of the associated plant that has or may have the associated actual or potential pest or disease.

22. The non-transitory computer readable medium of claim 21, wherein the graphical user interface comprises:
a summary section displayed adjacent to the image and providing details related to the at least one first indicator identifying the at least one of the one or more actual or potential pests or diseases.

23. The non-transitory computer readable medium of claim 21, wherein the graphical user interface comprises:
a two-dimensional or three-dimensional representation of at least part of the growing area; and
at least one third indicator identifying the at least one of the one or more actual or potential pests or diseases, each third indicator placed in the representation in association with a location of the associated plant that has or may have the associated actual or potential pest or disease.

24. The non-transitory computer readable medium of claim 21, wherein the graphical user interface comprises at least some of the stereo-spatio-temporal data measurements in a spatial overview of the growing area and additional information related to the growing area.

25. The non-transitory computer readable medium of claim 21, further containing instructions that when executed cause the at least one processor to identify one or more corrective actions that at least partially resolve the one or more actual or potential pests or diseases associated with the one or more plants.

26. The non-transitory computer readable medium of claim 25, wherein the graphical user interface comprises at least one third indicator identifying at least one of the one or more corrective actions, each third indicator placed in the graphical user interface in association with the associated plant to which the associated corrective action is to be applied.

27. The non-transitory computer readable medium of claim 21, further containing instructions that when executed cause the at least one processor to identify at least one of the one or more actual or potential pests or diseases based on a flux or a difference in a specified plant-related characteristic along at a plurality of heights of one or more of the plants.

28. The non-transitory computer readable medium of claim 21, further containing instructions that when executed cause the at least one processor to identify, for each of the one or more actual or potential pests or diseases, a portion of the associated plant that is or may be suffering from the associated actual or potential pest or disease.

29. The non-transitory computer readable medium of claim 28, wherein the instructions when executed cause the at least one processor to identify, for each actual or potential pest or disease, a corrective action to be applied to the portion of the plant that is or may be suffering from the associated actual or potential pest or disease.

30. The non-transitory computer readable medium of claim 21, wherein at least some of the first and second spatio-temporal data measurements comprise human observation data measurements.

* * * * *

UNITED STATES PATENT AND TRADEMARK OFFICE
CERTIFICATE OF CORRECTION

PATENT NO. : 12,067,711 B2
APPLICATION NO. : 17/098172
DATED : August 20, 2024
INVENTOR(S) : Humpston et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Twelfth Day of November, 2024

Katherine Kelly Vidal
*Director of the United States Patent and Trademark Office*